United States Patent
Disney et al.

(10) Patent No.: US 9,719,191 B2
(45) Date of Patent: Aug. 1, 2017

(54) METHODS FOR IDENTIFYING LIGANDS THAT TARGET NUCLEIC ACID MOLECULES AND NUCLEIC ACID STRUCTURAL MOTIFS

(75) Inventors: Matthew D. Disney, Williamsville, NY (US); Jessica L. Childs-Disney, Williamsville, NY (US)

(73) Assignee: The Research Foundation for The State University of New York, Buffalo, NY (US)

( * ) Notice: Subject to any disclaimer, the term of this patent is extended or adjusted under 35 U.S.C. 154(b) by 1264 days.

(21) Appl. No.: 11/998,466

(22) Filed: Nov. 29, 2007

(65) Prior Publication Data

US 2008/0188377 A1    Aug. 7, 2008

Related U.S. Application Data

(60) Provisional application No. 60/861,630, filed on Nov. 29, 2006.

(51) Int. Cl.
| | | |
|---|---|---|
| *C40B 30/04* | (2006.01) | |
| *C40B 20/08* | (2006.01) | |
| *C12Q 1/68* | (2006.01) | |
| *C40B 40/08* | (2006.01) | |
| *G01N 33/53* | (2006.01) | |
| *G01N 33/68* | (2006.01) | |
| *C40B 40/12* | (2006.01) | |

(52) U.S. Cl.
CPC ............ *C40B 20/08* (2013.01); *C12Q 1/6811* (2013.01); *C40B 30/04* (2013.01); *C40B 40/08* (2013.01); *G01N 33/5308* (2013.01); *G01N 33/6845* (2013.01); *C40B 40/12* (2013.01)

(58) Field of Classification Search
CPC .................................................... C40B 30/04
USPC .......................................................... 506/9
See application file for complete search history.

(56) References Cited

U.S. PATENT DOCUMENTS

| | | | |
|---|---|---|---|
| 6,261,774 B1 * | 7/2001 | Pagratis et al. ................... 435/6 |
| 6,268,137 B1 * | 7/2001 | Szyf ...................... C07H 21/00 435/375 |
| 6,551,784 B2 | 4/2003 | Fodor et al. | |
| 2004/0235027 A1 | 11/2004 | Lam et al. | |

OTHER PUBLICATIONS

Ge (UPA, a universal protein array system for quantitative detection of protein-protein, protein-DNA, protein-RNA, and protein-ligand interactions, 2000, Nucleic Acids Research, vol. 28, pp. i-vii).*
Disney et al. (Aminoglycoside microarrays to explore interactions of antibiotics with RNAs and proteins, 2004, Chem. Eur. J., vol. 10, pp. 3308-3314, provide by applicants in IDS).*
Dufva et al. (Characterization of an inexpensive, non-toxic, and highly sensitive microarray substrate, 2004, Biotechniques, vol. 37, pp. 286-296, provided by applicants in IDS).*
Tok et al. (RNA aptamers that specifically bind to a 16S ribosomal RNA decoding region construct, 2000, Nucleic Acids Research, vol. 28, pp. 2902-2910).*
Skripkin et al., Mechanisms of Inhibition of in Vitro Dimerization of HIV Type I RNA by Sense and Anti-Sense Oligonucleotides, Journal of Biological Chemistry, 1996, 271(46), 28812-28817.*
Artsimovitch et al., Interaction of a Nascent RNA Structure with RNA Polymerase is Required for Haripin-Dependent Transcriptional Pausing But Not for Transcript Release, Genes & Development, 1998, 12, 3110-3122.*
Childs et al., A Small Molecule Microarray Platform to Select RNA Internal Loop-Ligand Interactions, ACS Chemical Biology, 2007, 2(11), 745-754.*
Patel et al., Structure, Recognition and Adaptive Binding in RNA Aptamer Complexes, J. Mol. Biol., 1997, 272, 645-664.*
Hiller et al., Using RNA Secondary Structures to Guide Sequence Motif Finding Towards Single-Standed Regions, 2006, 34(17) 1-10.*
Westhof et al., RNA Tertiary Structure, Encyclopedia of Analytical Chemistry, R.A, Meyers ed., 2000, 1-10.*
SantaLucia et al., The Thermodynamics of DNA Structural Motifs, Annu. Rev. Biophys. Biomol. Struct., 2004, 33, 415-440.*
Vincze et al., "Reaction of Diethyl Pyrocarbonate With Nucleic Acid Components. Bases and Nucleosides Derived From Guanine, Cytosine, and Uracil," Am. Chem. Soc., 95:2677-2682 (1973).
Woese et al., "Secondary Structure Model for Bacterial 16S Ribosomal RNA: Phylogenetic, Enzymatic and Chemical Evidence," Nucleic Acids Res., 8:2275-2293 (1980).
Zaug et al., "The Intervening Sequence RNA of Tetrahymena is an Enzyme," Science, 231:470-475 (1986).
Ehresman et al., "Probing the Structure of RNA in Solution," Nucleic Acids Res., 15:9109-9128 (1987).
Moazed et al. "Interaction of Antibiotics With Functional Sites in 16S Ribosomal RNA," Nature, 327:389-394 (1987).
Milligan et al., "Synthesis of Small RNAs Using T7 RNA Polymerase," Methods Enzymol., 180:51-62 (1989).
Puglisi et al., "Absorbance Melting Curves of RNA," Methods Enzymol.,180:304-325 (1989).
Antao et al., "A Thermodynamic Study of Unusually Stable RNA and DNA Hairpins," Nucleic Acids Res., 19:5901-5905 (1991).

(Continued)

*Primary Examiner* — Amy M Bunker
(74) *Attorney, Agent, or Firm* — Hodgson Russ LLP

(57) ABSTRACT

Disclosed are methods for identifying a nucleic acid (e.g., RNA, DNA, etc.) motif which interacts with a ligand. The method includes providing a plurality of ligands immobilized on a support, wherein each particular ligand is immobilized at a discrete location on the support; contacting the plurality of immobilized ligands with a nucleic acid motif library under conditions effective for one or more members of the nucleic acid motif library to bind with the immobilized ligands; and identifying members of the nucleic acid motif library that are bound to a particular immobilized ligand. Also disclosed are methods for selecting, from a plurality of candidate ligands, one or more ligands that have increased likelihood of binding to a nucleic acid molecule comprising a particular nucleic acid motif, as well as methods for identifying a nucleic acid which interacts with a ligand.

7 Claims, 11 Drawing Sheets

(56) References Cited

OTHER PUBLICATIONS

SantaLucia et al., "Structure of (rGGCGAGCC) 2 in Solution From NMR and Restrained Molecular Dynamics," Biochemistry, 32:12612-12623 (1993).
Joyce, "In vitro evolution of nucleic acids," Curr. Opin. Struct. Biol., 4:331-336 (1994).
Klug et al., "All You Wanted to Know About SELEX," Mol. Biol. Rep., 20:97-107 (1994).
Roestamadji et al.,"Loss of Individual Electrostatic Interactions Between Aminoglycoside Antibiotics and Resistance Enzymes as an Effective Means to Overcoming Bacterial Drug Resistance," J. Am. Chem. Soc., 117:11060-11069 (1995).
Wang et al., "Specific Binding of Aminoglcoside Antibiotics to RNA," Chem. Biol., 2:281-290 (1995).
Fourmy et al., "Structure of the A Site of *Escherichia coli* 16S Ribosomal RNA Complexed With an Aminoglycoside Antibiotic," Science, 274:1367-1371 (1996).
Lato et al., "Screening Chemical Libraries for Nucleic-Acid-Binding Drugs by in Vitro Selection: a Test Case with Lividomycin," Mol. Diversity, 2:103-110 (1996).
Park et al.,"Rapid Combinatorial Synthesis of Aminoglycoside Antibiotic Mimetics: Use of a Polyethylene Glycol-Linked Amine and a Neamine-Derived Aldehyde in Multiple Component Condensation as a Strategy for the Discovery of New Inhibitors of the HIV RNA Rev Responsive Element," J. Am. Chem. Soc., 118:10150-10155 (1996).
Recht et al., "RNA Sequence Determinants for Aminoglycoside Binding to an A-Site rRNA Model Oligonucleotide," J. Mol. Biol., 262:421-436 (1996).
Wu et al., "Solution Structure of (rGCGGACGC) 2 by Two-Dimensional NMR and the Iterative Relaxation Matrix Approach," Biochemistry, 35:9677-9689 (1996).
Hamy et al., "An Inhibitor of the Tat/TAR RNA Interaction That Effectively Suppresses HIV-1 Replication," Proc. Natl. Acad. Sci. U.S.A., 94:3548-3553 (1997).
Osborne et al., "Nucleic Acid Selection and the Challenge of Combinatorial Chemistry," Chem. Rev., 97:349-370 (1997).
Wang et al., "Specificity of Aminoglycoside Binding to RNA Constructs Derived from the 16S rRNA Decoding Region and the HIV-RRE Activator Region," Biochemistry, 36:768-779 (1997).
Bevilacqua et al., "Thermodynamic Analysis of an RNA Combinatorial Library Contained in a Short Hairpin," Biochemistry, 37:15877-15884 (1998).
SantaLucia,"A Unified View of Polymer, Dumbbell, and Oligonucleotide DNA Nearest-Neighbor Thermodynamics," Proc. Natl. Acad. Sci. U. S. A., 95:1460-1465 (1998).
Werstuck et al., "Controlling Gene Expression in Living Cells Through Small Molecule-RNA Interactions," Science, 282:296-298(1998).
Wong et al.,"Specificity of Aminoglycoside Antibiotics for the A-Site of the Decoding Region of Ribosomal RNA," Chem. Biol., 5:397-406 (1998).
Batey et al., "Tertiary Motifs in RNA Structure and Folding," Angew. Chem., Int. Ed. Engl., 38:2326-2343 (1999).
Griffey et al., "Determinants of Aminoglycoside-Binding Specificity for rRNA by Using Mass Spectrometry," Proc. Natl. Acad. Sci. U.S.A., 96:10129-10133 (1999).
Harada et al., "Screening Rna-Binding Libraries Using a Bacterial Transcription Antitermination Assay," Methods Mol. Biol., 118:177-187 (1999).
Kirk et al., "tRNA(Phe) Binds Aminoglycoside Antibiotics," Bioorg. Med. Chem., 7:1979-1991 (1999).
MacBeath et al., "Printing Small Molecules as Microarrays and Detecting Protein-ligand Interactions En Masse," J. Am. Chem. Soc., 121:7967-7968 (1999).
Mathews et al., "Expanded Sequence Dependence of Thermodynamic Parameters Improves Prediction of RNA Secondary Structure," J. Mol. Biol., 288:911-940 (1999).
Peyret et al., "Nearest-Neighbor Thermodynamics and NMR of DNA Sequences With Internal A.A, C.C, and T.T Mismatches," Biochemistry, 38:3468-3477 (1999).
Shu et al., "Isolation and Characterization of Thermodynamically Stable and Unstable RNA Hairpins From a Triloop Combinatorial Library," Biochemistry, 38:15369-15379 (1999).
Afanassiev et al., "Preparation of DNA and Protein Micro Arrays on Glass Slides Coated with an Agarose Film," Nucleic Acids Res., 28:E66 (2000).
Cho et al., "Specific Binding of Hoechst 33258 to Site 1 Thymidylate Synthase mRNA Aminoglycoside Antibiotics are Able to Specifically Bind the 5=-untranslated Region of Thymidylate Synthase Messenger RNA," Nucleic Acids Res., 28: 2158-2163 (2000).
Disney et al., "Targeting a Pneumocystis Carinii Group I Intron With Methylphosphonate Oligonucleotides: Backbone Charge Is Not Required for Binding or Reactivity," Biochemistry, 39:6991-7000 (2000).
Doudna, "Structural Genomics of RNA," Nat. Struct. Biol., 7 (Suppl.):954-956 (2000).
MacBeath et al.,"Printing Proteins as Microarrays for High-Throughput Function Determination," Science, 289:1760-1763 (2000).
Dervan, "Molecular Recognition of DNA by Small Molecules," Bioorg. Med. Chem., 9:2215-2235 (2001).
Gallego et al., "Targeting RNA with Small Molecule Drugs: Therapeutic Promise and Chemical Challenges," Acc. Chem. Res., 34:836-843 (2001).
Kolb et al., "Click Chemistry: Diverse Chemical Function from a Few Good Reactions," Angew. Chem., Int. Ed. Engl., 40:2004-2021 (2001).
Lagos-Quintana et al., "Identification of Novel Genes Coding for Small Expressed RNAs," Science, 294:853-858 (2001).
Sreedhara et al., "Targeted Site-Specific Cleavage of HIV-1 Viral Rev Responsive Element by Copper Aminoglycosides," J. Biol. Inorg. Chem., 6:166-172 (2001).
Llano-Sotelo et al., "Aminoglycosides Modified by Resistance Enzymes Display Diminished Binding to the Bacterial Ribosomal Aminoacyl-tRNA Site," Chem. Biol., 9: 455-463 (2002).
Proctor et al., "Isolation and Characterization of a Family of Stable RNA Tetraloops with the Motif YNMG That Participate in Tertiary Interactions," Biochemistry, 41:12062-12075 (2002).
Swayze et al., "SAR by MS: A Ligand Based Technique for Drug Lead Discovery Against Structured Rna Targets," J. Med. Chem.,45:3816-3819 (2002).
Winkler et al., "Thiamine Derivatives Bind Messenger RNAs Directly to Regulate Bacterial Gene Expression," Nature, 419:952-956(2002).
Yoshizawa et al. "Sequence-specific Recognition of the Major Groove of RNA by Deoxystreptamine," Biochemistry, 41: 6263-6270 (2002).
Carlson et al., "Preferred RNA Binding Sites for a Threading Intercalator Revealed by in Vitro Evolution," Chem. Biol., 10:663-672 (2003).
Carter et al., "X Functional Insights From the Structure of the 30S Ribosomal Subunit and its Interactions With Antibiotics," Nature, 407:340-348 (2003).
Johnson et al., "Application of NMR SHAPES Screening to an RNA Target," J. Am. Chem. Soc., 125:15724-15725 (2003).
Kolb et al., "The Growing Impact of Click Chemistry on Drug Discovery," Drug Discovery Today, 8:1128-1137 (2003).
Krebs et al., "Targeting the HIV Trans-Activation Responsive Region-Approaches Towards RNA-Binding Drugs," ChemBioChem, 4:972-978 (2003).
Lynch et al., "Comparison of X-ray Crystal Structure of the 30S Subunit-Antibiotic Complex with NMR Structure of Decoding Site Oligonucleotide-Paromomycin Complex," Structure, 11:43-53 (2003).
Tor et al.,"Targeting RNA With Small Molecules," ChemBioChem, 4:998-1007 (2003).
Chan et al., "Polytriazoles as Copper(i)-Stabilizing Ligands in Catalysis," Org. Lett., 6:2853-2855 (2004).

(56) References Cited

OTHER PUBLICATIONS

Denap et al., "Combating Drug-Resistant Bacteria: Small Molecule Mimics of Plasmid Incompatibility as Antiplasmid Compounds," J. Am. Chem. Soc., 126:15402-15404 (2004).

Disney et al.,"Aminoglycoside Microarrays to Explore Interactions of Antibiotics with RNAs and Proteins," Chemistry, 10:3308-3314 (2004).

Disney et al.,"Aminoglcoside Microarrays to Study Antibiotic Resistance," Angew. Chem. Int. Ed. Engl.,43:1591-1594 (2004).

Disney et al., "The Use of Carbohydrate Microarrays to Study Carbohydrate-Cell Interactions and to Detect Pathogens," Chem. Biol., 11:1701-1707 (2004).

Dufva et al., "Characterization of an Inexpensive, Nontoxic, and Highly Sensitive Microarray Substrate," Biotechniques, 37:286-296 (2004).

He et al., "Synthesis and Evaluation of Novel Bacterial rRNA-Binding Benzimidazoles by Mass Spectrometry," Bioorg. Med. Chem. Lett., 14:695-699 (2004).

Kaul et al., "Fluorescencebased Approach for Detecting and Characterizing Antibiotic-Induced Conformational Changes in Ribosomal RNA: Comparing Aminoglycoside Binding to Prokaryotic and Eukaryotic Ribosomal RNA Sequences," J. Am. Chem. Soc., 126:3447-3453 (2004).

Mathews et al., "Incorporating Chemical Modification Constraints into a Dynamic Programming Algorithm for Prediction of RNA Secondary Structure," Proc. Natl. Acad. Sci. U.S.A., 101:7287-7292 (2004).

Mendons et al., "In Vitro Evolution of Functional DNA Using Capillary Electrophoresis," J. Am. Chem. Soc., 126: 20-21 (2004).

Ratner et al., "Tools for Glycomics: Mapping Interactions of Carbohydrates in Biological Systems," ChemBioChem, 5: 1375-1383 (2004).

Shandrick et al., "Monitoring Molecular Recognition of the Ribosomal Decoding Site," Angew. Chem., Int. Ed. Engl., 43: 3177-3182 (2004).

Seth et al., "SAR by MS: Discovery of a New Class of RNA-binding Small Molecules for the Hepatitis C Virus: Internal Ribosome Entry Site IIA Subdomain," J. Med. Chem., 48:7099-7102 (2005).

Thomas et al., "Size-Specific Ligands for RNA Hairpin Loops," J. Am. Chem. Soc.,127:12434-12435 (2005).

Thomas et al., "The Relationship Between Aminoglycosides' RNA Binding Proclivity and Their Antiplasmid Effect on an IncB Plasmid Combating Drug-Resistant Bacteria: Small Molecule Mimics of Plasmid Incompatibility as Antiplasmid Compounds," Biochemistry, 44:6800-6808 (2005).

Barrett et al.,"Chemical Microarrays to Identify Ligands That Bind Pathogenic Cells," ChemBioChem,7:1882-1885 (2006).

Kaul et al., "Aminoglycosideinduced Reduction in Nucleotide Mobility at the Ribosomal RNA A-Site as a Potentially Key Determinant of Antibacterial Activity," J. Am. Chem. Soc., 128:1261-1271 (2006).

Thomas et al., "Biochemical and Thermodynamic Characterization of Compounds That Bind to RNA Hairpin Loops: Toward an Understanding of Selectivity," Biochemistry, 45:10928-10938 (2006).

Childs-Disney et al., "A Small Molecule Microarray Platform to Select RNA Internal Loop-Ligand Interactions.," ACS Chem Biol., 2(11):745-754 (2007).

Disney et al., "An Aminoglycoside Microarray Platform for Directly Monitoring and Studying Antibiotic Resistance," Biochemistry, 40:11223-11230 (2007).

Disney et al., "Using Selection to Identify and Chemical Microarray to Study the RNA Internal Loops Recognized by 6'-N-Acylated Kanamycin A," ChemBioChem, 8:649-656 (2007).

* cited by examiner

*Fig. 2*
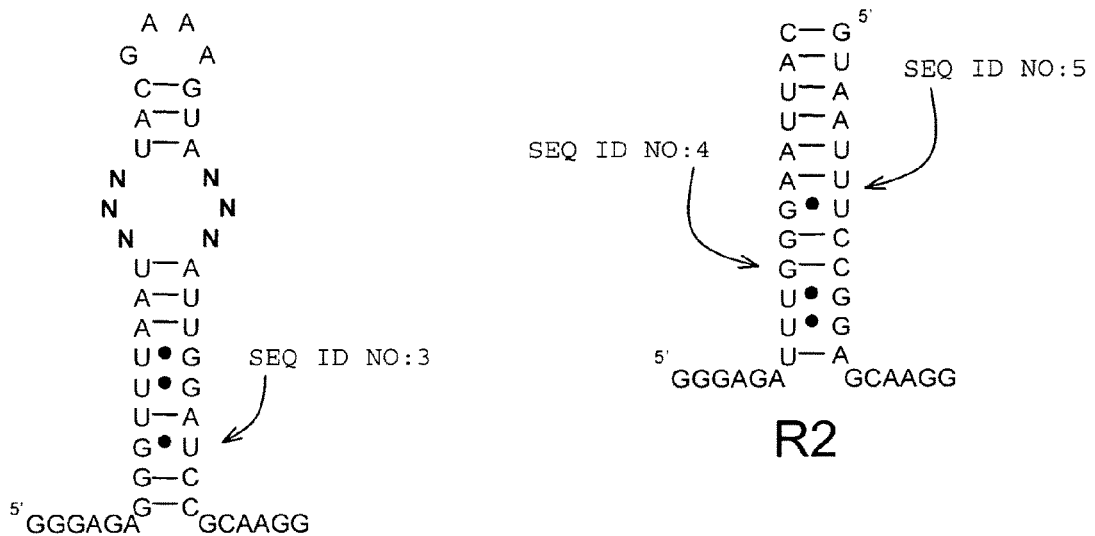
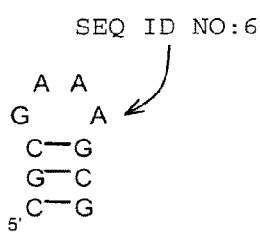
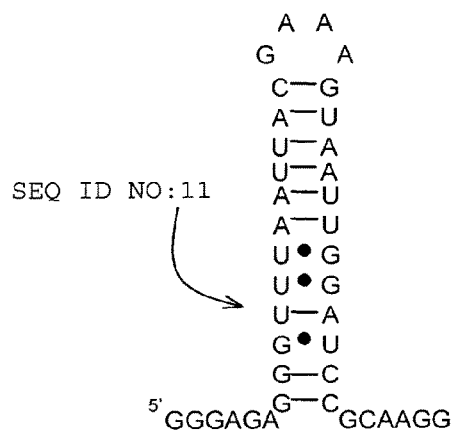

*Fig. 3*

```
        A  A
      G    A
      C—G
     ┌A—U┐
     │U—A│
     │N  N│
     │N  N│
     │N  N│
     │U—A│
     └A—U┘
      A—U
      U•G
      U•G
      U—A
      G•U
      G—C
5'GGGAGA G—C GCAAGG
         C
    SEQ ID NO:3
```

| | |
|---|---|
| R1 | 110±2 |
| R2 | >500 |
| R3 | >500 |
| D1+D2 | ~500 |
| R4 | ~300 |
| tRNA[a] | ~500 |

```
   A—U
   U—A
   U—A
   U   C
   U   U
   U—A
5' A—U
   IL 1
 2.2 ± 0.2
SEQ ID NO:12
```

```
   A—U
   U—A
   U—A
   U   C
   C   U
   U—A
5' A—U
   IL 2
 3.3 ± 0.1
SEQ ID NO:13
```

```
   A—U
   U—A
   U—A
   U   U
   A—U
   U—A
5' A—U
   IL 3
 3.6 ± 0.4
SEQ ID NO:14
```

```
   A—U
   U—A
   U—A
   A   A
   G•U
   U—A
5'A—U
   IL 4
 3.7±0.3
SEQ ID NO:15
```

```
   A—U
   U—A
   A   C
   U   U
   C   A
   U—A
5' A—U
   IL 5
 4.8±0.2
SEQ ID NO:16
```

```
   A—U
   U—A
   U—A
   A   A
   G   G
   U—A
5'A—U
   IL 6
 5.5±0.7
SEQ ID NO:17
```

```
   A—U
   U—A
   G—C
   G•U
   C   U
   U—A
5' A—U
   IL 7
 7.2±0.7
SEQ ID NO:18
```

```
   A—U
   U—A
   U—A
   C   A
   C—G
   U—A
5' A—U
   IL 8
 7.4±0.7
SEQ ID NO:19
```

```
   A—U
   U—A
   C   A
   G   C
   C   A
   U—A
5' A—U
   IL 9
 8.6±0.6
SEQ ID NO:20
```

```
   A—U
   U—A
   A   A
   A   U
   G   A
   U—A
5'A—U
   IL 10
 9.6±0.8
SEQ ID NO:21
```

```
   A—U
   U—A
   U   C
   A—U
   U—A
   U—A
5' A—U
   IL 11
10.0±0.6
SEQ ID NO:22
```

```
   A—U
   U—A
   C—G
   C   U
   U—A
5'A—U
   IL 12
10.9±0.4
SEQ ID NO:23
```

```
   A—U
   U—A
   C—G
   G—C
   G•U
   G   A
   U—A
5' A—U
   IL 13
11.7±0.2
SEQ ID NO:24
```

```
   A—U
   U—A
   G•U
   U•G
   C   A
   C—G
   U—A
5' A—U
   IL 14
13.0±0.2
SEQ ID NO:25
```

```
   A—U
   U—A
   U—A
   A   G
   A—U
   U—A
5' U—A
   IL 15
13.2±0.5
SEQ ID NO:26
```

```
   A—U
   U—A
   A   C
   G   G
   U—A
   U—A
5'A—U
   IL 16
20.0±0.8
SEQ ID NO:27
```

```
   A—U
   U—A
   U   C
   U   C
   C—G
   U—A
5' A—U
   IL 17
20.1±0.9
SEQ ID NO:28
```

```
   A—U
   U—A
   G   G
   A   A
   U   U
   U—A
5'A—U
   IL 18
27.5±0.8
SEQ ID NO:29
```

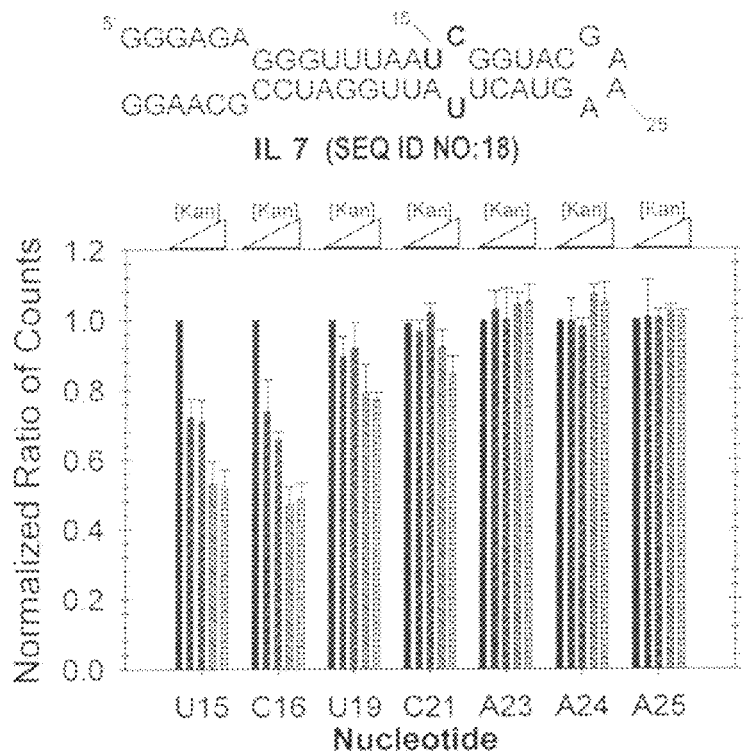
*Fig. 6A*
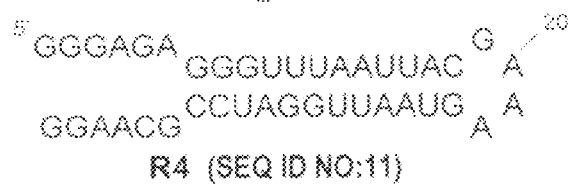
*Fig. 6B*
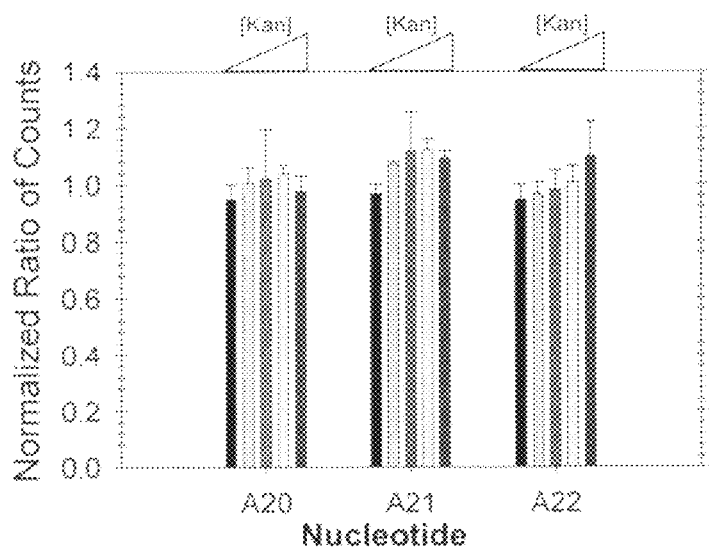

Mechanical Removal of Bound RNA

*Fig. 9*
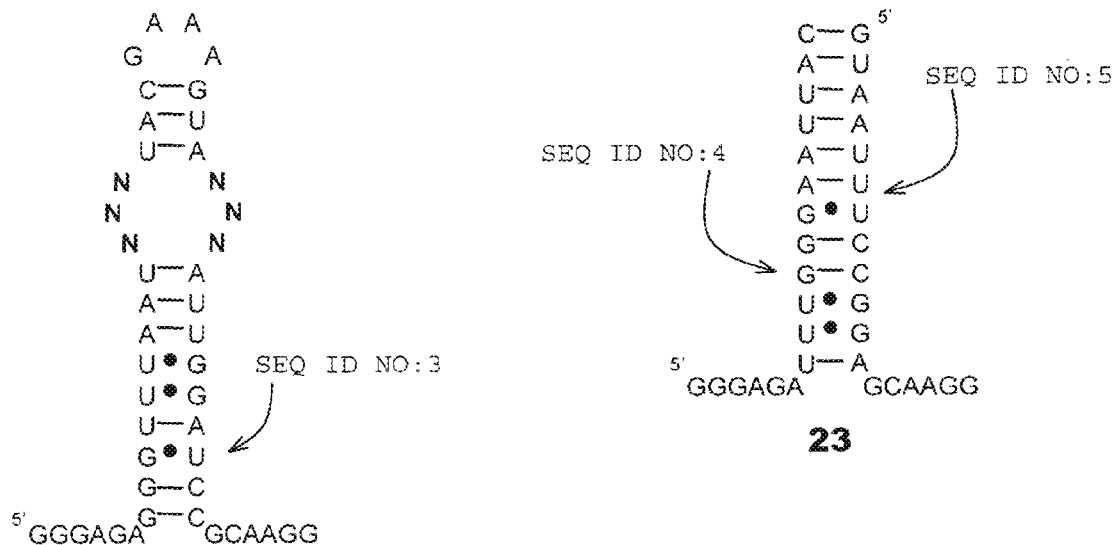
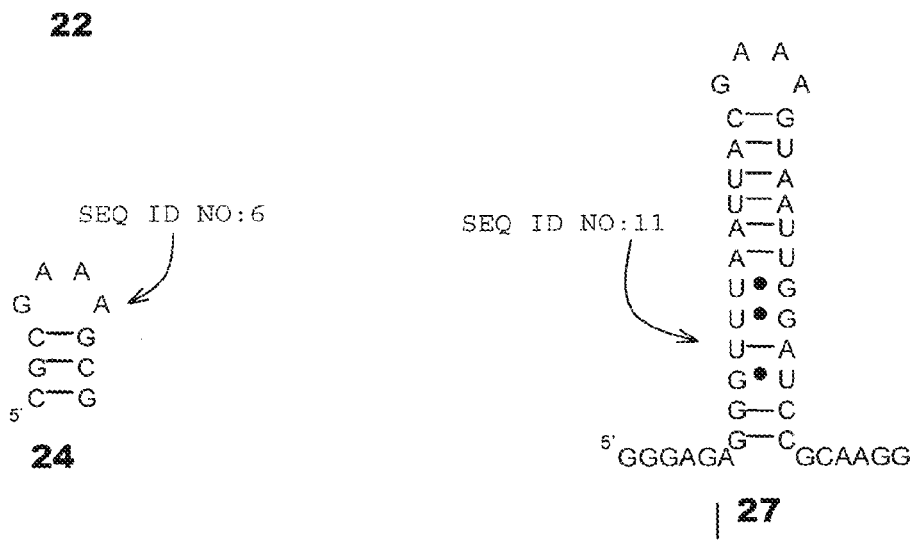

Fig. 12

IL 21 (5 ± 3, SEQ ID NO:30)
```
A—U
U—A
U•G
U—A
C   A
U—A
A—U
```

IL 22 (5 ± 1, SEQ ID NO:31)
```
A—U
U—A
G   G
A—U
U•G
U—A
A—U
```

IL 23 (8 ± 2, SEQ ID NO:32)
```
A—U
U—A
A—U
A   C
G•U
U—A
A—U
```

IL 24 (10 ± 3, SEQ ID NO:33)
```
A—U
U—A
C—G
U•G
C   C
U—A
A—U
```

IL 25 (12 ± 3, SEQ ID NO:34)
```
A—U
U—A
G•U
A   C
U•G
U—A
A—U
```

IL 26 (5 ± 2, SEQ ID NO:35)
```
A—U
U—A
G•U
A   G
C   A
U—A
A—U
```

IL 27 (11 ± 5, SEQ ID NO:36)
```
A—U
U—A
A   C
U   U
U—A
U—A
A—U
```

IL 28 (16 ± 6, SEQ ID NO:37)
```
A—U
U—A
A—U
A   G
G   A
U—A
A—U
```

IL 29 (20 ± 2, SEQ ID NO:38)
```
A—U
U—A
C   C
A   C
U•G
U—A
A—U
```

IL 30 (20 ± 8, SEQ ID NO:39)
```
A—U
U—A
U•G
C   C
C   C
U—A
A—U
```

IL 31 (22 ± 6, SEQ ID NO:40)
```
A—U
U—A
C   U
A   C
U•G
U—A
A—U
```

IL 32 (6 ± 1, SEQ ID NO:41)
```
A—U
U—A
G   G
G   A
G   G
U—A
A—U
```

IL 33 (8 ± 3, SEQ ID NO:42)
```
A—U
U—A
G   G
A   C
A   G
U—A
A—U
```

IL 34 (9 ± 3, SEQ ID NO:43)
```
A—U
U—A
C   A
G   U
A   C
U—A
A—U
```

IL 35 (11 ± 1, SEQ ID NO:44)
```
A—U
U—A
A   G
U   G
G   G
U—A
A—U
```

IL 36 (12 ± 2, SEQ ID NO:45)
```
A—U
U—A
U   U
C   A
C   A
U—A
A—U
```

METHODS FOR IDENTIFYING LIGANDS THAT TARGET NUCLEIC ACID MOLECULES AND NUCLEIC ACID STRUCTURAL MOTIFS

The present application claims the benefit of U.S. Provisional Patent Application Ser. No. 60/861,630, filed Nov. 29, 2006, which provisional patent application is hereby incorporated by reference.

STATEMENT AS TO FEDERALLY SPONSORED RESEARCH

This invention was made with Government support under contract number NNA05CS96G awarded by NASA. The Government has certain rights in the invention.

FIELD OF THE INVENTION

The present invention relates to methods and materials for systematically identifying RNA-ligand interactions, and, more particularly, to methods and materials that can be used to identify small molecules that target particular RNA motifs.

The present application cites a number of references, some or all of which are cited by number in square brackets. The references thus cited are listed in a section entitled "References" immediately before the claims. Each reference cited in this application, whether by number or otherwise, is hereby incorporated in its entirety, by reference.

BACKGROUND OF THE INVENTION

RNA forms complex tertiary structures that impart diverse functions [1,2]. For example, RNA catalyzes reactions [3], regulates gene expression [4, 5], encodes protein, and plays other essential roles in biology. Therefore, RNA is an interesting and important target for developing drugs or probes of function [6,7]. It is a vastly underutilized target, however, mainly because of the limited information available on RNA ligand interactions that could facilitate rational design.

One advantage of using RNA as a drug target is that secondary structure information, which includes the motifs that comprise an RNA, can be easily obtained from sequence by free energy minimization [8,9] or phylogenic comparison [10]. RNA tertiary structures are composites of the secondary structural motifs and the long-range contacts that form between them. Furthermore, RNA motifs can have similar properties both as isolated systems and as parts of larger RNAs. For example, aminoglycoside antibiotics affect the structure of the bacterial rRNA A-site similarly when they bind the entire ribosome or an oligonucleotide mimic of the bacterial rRNA A-site [11-16]. Studies on the binding of aminoglycosides and streptamine dimers to RNA hairpins [17-20] have facilitated the development of compounds to combat multidrug resistance by causing plasmid incompatibility [19, 20]. These results show that the identification of RNA motifs that bind small molecules can be useful for targeting the larger RNAs that contain them.

However, since RNA can adopt diverse structures, internal and hairpin loops for example, an understanding how to target RNA with small molecules and other ligands has not yet been achieved. Current methods to study and identify RNA ligand interactions include systematic evolution of ligands by exponential enrichment ("SELEX") [21, 22], structure-activity relation-ships ("SAR") by mass spectrometry ("MS") [23-26] and NMR [27], and chemical microarrays [28-30]. These methods probe RNA space (SELEX) or chemical space (SAR by MS and NMR and chemical microarrays) separately. However, these methods do not permit a systematic study of RNA-ligand interactions.

For all of the above reasons, a need exists for methods that can be used to systematically identify RNA-ligand interactions, and the present invention is directed, in part, to addressing this need.

SUMMARY OF THE INVENTION

The present invention relates to a method for identifying a nucleic acid motif which interacts with a ligand. The method includes providing a plurality of ligands immobilized on a support, wherein each particular ligand is immobilized at a discrete location on the support; contacting the plurality of immobilized ligands with a nucleic acid motif library under conditions effective for one or more members of the nucleic acid motif library to bind with the immobilized ligands; and identifying members of the nucleic acid motif library that are bound to a particular immobilized ligand.

The present invention also relates to a method for selecting, from a plurality of candidate ligands, one or more ligands that have increased likelihood of binding to a nucleic acid molecule comprising a particular nucleic acid motif. The method includes providing a database which correlates various ligands' abilities to bind to the particular nucleic acid motif and various other nucleic acid motifs; comparing the candidate ligands' ability to bind to the particular nucleic acid motif; and choosing one or more ligands based on their ability to bind to the particular nucleic acid motif.

The present invention also relates to a method for selecting, from a plurality of candidate ligands, one or more ligands that have increased likelihood of binding to a first nucleic acid molecule comprising a first particular nucleic acid motif and that have decreased likelihood of binding to a second nucleic acid molecule comprising a second particular nucleic acid motif. The method includes providing a database which correlates various ligands' abilities to bind to the first particular nucleic acid motif, to the second particular nucleic acid motif, and to various other nucleic acid motifs; comparing the candidate ligands' ability to bind to the first particular nucleic acid motif and to the second particular nucleic acid motif; and choosing one or more ligands based on their ability to bind to the first particular nucleic acid motif and their inability to the second particular nucleic acid motif.

The present invention also relates to a method for identifying a nucleic acid which interacts with a ligand. The method includes providing a plurality of ligands immobilized on a support, wherein each particular ligand is immobilized at a discrete location on the support; contacting the plurality of immobilized ligands with a nucleic acid library under conditions effective for one or more members of the nucleic acid library to bind with the immobilized ligands; and identifying members of the nucleic acid library that are bound to a particular immobilized ligand.

BRIEF DESCRIPTION OF THE DRAWINGS

FIG. 2 is a drawing showing the sequence and structure of oligonucleotides that can be used in the methods of the present invention. R1 (SEQ ID NO:3) is an RNA motif library displaying a random 3×3 internal loop in which N refers to a random mixture of A, C, G, and U. R2, R3, D1, and D2 are chase oligonucleotides. Structure R2 is a duplex (SEQ ID NO:4 and SEQ ID NO:5) that is related to the stems of R1; R3 (SEQ ID NO:6) is a short hairpin having the hairpin sequence and closing base pair of R1; D1 (SEQ ID NO:7 and SEQ ID NO:8) and D2 (SEQ ID NO:9 and SEQ ID NO:10) are DNA chase oligonucleotides. The RNA R4 (SEQ ID NO:11) is the cassette into which the library was inserted as shown in R1.

FIG. 3 is a drawing showing the secondary structure of the RNA internal loops and the closing base pairs that were selected to bind immobilized kanamycin A using a method according to the present invention. Secondary structures were modeled using free energy minimization using the program RNAStructure. The internal loop library (R1 (SEQ ID NO:3)) is shown at the upper left, and the boxed nucleotides are shown on the right for the selected internal loops ("IL") that bind to kanamycin A (i.e., IL 1 (SEQ ID NO:12), IL 2 (SEQ ID NO:13), IL 3 (SEQ ID NO:14), IL 4 (SEQ ID NO:15), IL 5 (SEQ ID NO:16), IL 6 (SEQ ID NO:17), IL 7 (SEQ ID NO:18), IL 8 (SEQ ID NO:19), IL 9 (SEQ ID NO:20), IL 10 (SEQ ID NO:21), IL 11 (SEQ ID NO:22), IL 12 (SEQ ID NO:23), IL 13 (SEQ ID NO:24), IL 14 (SEQ ID NO:25), IL 15 (SEQ ID NO:26), IL 16 (SEQ ID NO:27), IL 17 (SEQ ID NO:28), IL 18 (SEQ ID NO:29). Values under each loop represent the $IC_{50}$ (nM). Values under internal loop library R1 are the $IC_{50}$ (nM) values for R1 (random), for chase oligonucleotides R2, R3, D1, and D2, for cassette R4, and for bulk tRNA from yeast.

FIG. 4A shows a reaction of FITC-labeled 6'-N-5-hexynoate neamine with azide displaying agarose slides under click chemistry conditions. The reaction was not analyzed for its isomeric content, and, therefore, a single FITC isomer is drawn for simplicity. FIG. 4B is an image of an array after reaction of FITC-labeled 6'-N-5-hexynoate neamine with azide displaying agarose slides with a variety of conditions. The concentrations of each component in these reactions are 5 mM sodium ascorbate, 1 mM $CuSO_4$, 100 μM TBTA, and 80 μM of 6'-N-5-hexynoate neamine-Fl.

FIGS. 6A and 6B are bar graphs showing nuclease mapping results in the presence and absence of 6' hexynoate kanamycin A. Bold nucleotides are protected from modification in the presence of compound. FIG. 6A shows that binding with IL 7 (SEQ ID NO:18) occurs only in the randomized regions from the original library. FIG. 6B shows that no nucleotides are protected from modification in the hairpin cassette (R4) (SEQ ID NO:11). Plots are ratio of counts for each nucleotide as a function of 6' hexynoate kanamycin A. The concentrations of compound are 0, 0.1, 1, 10, and 100 μM.

FIG. 9 is a drawing showing the sequence and structure of oligonucleotides that can be used in the methods of the present invention. Oligonucleotide 22 (SEQ ID NO:3) is an RNA motif library (internal loop library) with six randomized positions (N). The library has 4096 unique members. Oligonucleotides 23, 24, 25, and 26 are chase oligonucleotides. Oligonucleotide 23 is a duplex (SEQ ID NO:4 and SEQ ID NO:5) that is a mimic of the stems of 22. The sequence in 23 was altered such that it does not compete for RT-PCR primers. Oligonucleotide 24 (SEQ ID NO:6) is a mimic of the GAAA hairpin in 22. Oligonucleotides 25 (SEQ ID NO:7 and SEQ ID NO:8) and 26 (SEQ ID NO:9 and SEQ ID NO:10) are DNA chase oligonucleotides that ensure that interactions are RNA specific. The RNA 27 (SEQ ID NO:11) is the cassette in which the internal loop library is embedded. Oligonucleotides 23-26 were used at 1000 times the concentration of 22 in selection experiments to ensure that interactions occurred to loop nucleotides and not to the cassette.

FIG. 11A is an image of an array after hybridization with $^{32}$P-labeled 22 and unlabeled 23-26. Bound RNAs were mechanically removed from the agarose surface at the positions indicated with the circle. FIG. 11B shows the results from RT-PCR amplification of the samples removed in A. "N.C." refers to a negative control RT-PCR reaction from background or nonaminoglycoside functionalized agarose. FIG. 11C shows structures of the four azido-aminoglycosides (28-31) that were anchored onto alkyne-functionalized agarose and probed for binding to the RNA library. By screening four compounds at five loadings for binding 21, we probed 4×4096, or 16,382, interactions in duplicate when we only consider the different compounds or 4×5×4096, or 81,920, interactions in duplicate when we consider both the compounds and their loadings.

FIG. 12 is a drawing showing the secondary structures of the internal loops selected to bind 21. The secondary structures were the lowest free energy structures predicted by the program RNAStructure (R8, R9). The nucleotides shown are derived from the boxed region in 22 (FIG. 3). The selected internal loops (library members) were: IL 21 (SEQ ID NO:30), IL 22 (SEQ ID NO:31), IL 23 (SEQ ID NO:32), IL 24 (SEQ ID NO:33), IL 25 (SEQ ID NO:34), IL 26 (SEQ ID NO:35), IL 27 (SEQ ID NO:36), IL 28 (SEQ ID NO:37), IL 29 (SEQ ID NO:38), IL 30 (SEQ ID NO:39), IL 31 (SEQ ID NO:40), IL 32 (SEQ ID NO:41), IL 33 (SEQ ID NO:42), IL 34 (SEQ ID NO:43), IL 35 (SEQ ID NO:44), and IL 36 (SEQ ID NO:45). The dissociation constants (nM) were determined from fluorescence assays. The $K_d$ values for oligonucleotides 22, 23, 24, 25+26, and 27 are 280 nM, >5 µM, >5 µM, >5 µM, and 1.3 µM, respectively. The $K_d$ for tRNA$^{phe}$ is 0.7 µM. For each selected internal loop, the binding curves indicate a stoichiometry of 1:1.

DETAILED DESCRIPTION OF THE INVENTION

Figure 1A:
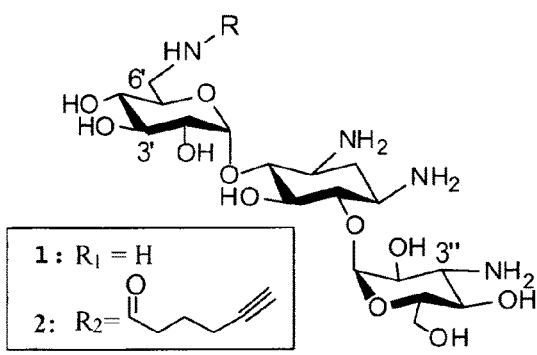
FIG. 1A is a drawing showing the structures of small molecule ligands that can be used in the methods of the present invention. 1 is kanamycin A and 2 is 6'-N-5-hexynoate kanamycin A that was used in chemical microarray-based assays to study binding to selected RNA internal loops.

The present invention relates to a method for identifying a nucleic acid motif which interacts with a ligand. The method includes providing a plurality of ligands immobilized on a support, wherein each particular ligand is immobilized at a discrete location on the support; contacting the plurality of immobilized ligands with a nucleic acid motif library under conditions effective for one or more members of the nucleic acid motif library to bind with the immobilized ligands; and identifying members of the nucleic acid motif library that are bound to a particular immobilized ligand.

"Nucleic acid", as used herein, is meant to refer to RNA and DNA. "RNA", as used herein, is meant to refer to ribonucleic acid molecules and oligomers. "DNA", as used herein, is meant to refer to deoxyribonucleic acid molecules and oligomers.

"Nucleic acid motif", as used herein, is meant to refer to a targetable internal loop, hairpin loop, bulge, or other targetable nucleic acid structural motifs. "Nucleic acid motif" are meant to include RNA motifs, for example, as described in Batey et al., "Tertiary Motifs in RNA Structure and Folding," *Angew. Chem. Int. Ed.*, 38:2326-2343 (1999), which is hereby incorporated by reference. Examples of RNA motifs include symmetric internal loops, asymmetric internal loops, 1×1 internal loops, 1×2 internal loops, 1×3 internal loops, 2×2 internal loops, 2×3 internal loops, 2×4 internal loops, 3×3 internal loops, 3×4 internal loops, 4×4 internal loops, 4×5 internal loops, 5×5 internal loops, 1 base bulges, 2 base bulges, 3 base bulges, 4 base bulges, 5 base bulges, 4 base hairpin loops, 5 base hairpin loops, 6 base hairpin loops, 7 base hairpin loops, 8 base hairpin loops, 9 base hairpin loops, 10 base hairpin loops, multibranch loops, pseudoknots, etc. Examples of DNA motifs include symmetric internal loops, asymmetric internal loops, bulges, and hairpin loops.

"Ligand", as used herein, is meant to refer to non-nucleic acid compounds that may be capable of binding to or otherwise interacting with one or more nucleic acids or nucleic acid motifs. Examples of ligands include proteins, polypeptides, carbohydrates, and other non-nucleic acid biopolymers; whole cells; and small molecules. "Small molecules", as used herein, are meant to refer to non-biopolymer compounds having, for example, a molecular weight of less than 10,000 grams/mole, such as less than 9000 grams/mole, less than 8000 grams/mole, less than 7000 grams/mole, less than 6000 grams/mole, less than 5000 grams/mole, less than 4000 grams/mole, less than 3000 grams/mole, less than 2000 grams/mole, less than 1000 grams/mole, less than 900 grams/mole, less than 800 grams/mole, less than 700 grams/mole, less than 600 grams/mole, less than 500 grams/mole, less than 400 grams/mole, etc.) that may be capable of binding to or otherwise interacting with one or more nucleic acids or nucleic acid motifs. Examples of small molecules that can be used in the methods of the present invention include small molecule antibiotics, small molecule antiviral agents, small molecule antifungals, small molecule chemotherapeutics, and other small molecule drugs. The small molecules can be biological compounds or mixtures of such compounds (e.g., derived from plant, fungal, bacterial, algal, or other extracts); or they can be synthetic organic compounds; or they can be inorganic compounds (e.g., cisplatin). Pharmaceutical companies have extensive libraries of such small molecules that can be used in the methods of the present invention.

"Interacts", as used herein, is mean to refer to binding or other stabilized association between the ligand and the RNA motif. The association can be thermodynamically stabilized or kinetically stabilized or both, and the interaction can be the result of covalent bonding, hydrogen bonding, van der Waals interactions, electrostatic interactions, or combinations of these and/or other types of interactions.

The method includes providing a plurality of ligands immobilized on a support, each particular ligand being immobilized at a discrete location on the support. Illustratively, the ligands can be immobilized on the support's surface at discrete locations arranged in the form of an array. The choice of support is not particularly critical to the practice of the present invention. Agarose supports are suitable and, in some embodiments, may be optimal. Other suitable supports include sepharose supports, functionalized glass supports, polyacylamide supports, polylactic acid supports, polymaleic acid supports, and other solid supports. Ligands can be immobilized, for example, using standard immobilization chemistries, the selection of which will depend on the nature of the ligands being immobilized and the nature of the support. Such immobilization chemistries can involve covalently coupling the small molecule or other ligand to the support. For example, in cases where the support is an agarose support, the support can be functionalized with azide and alkyne-functionalized small molecules or other ligands can be immobilized via a Huisgen dipolar cycloaddition reaction. By way of further illustration, in cases where the ligands are small molecules or other ligands functionalized with azide moieties, immobilization can be effected using an alkyne-functionalized agarose support. Other chemistries can be employed, such as using silyl chloride functionalized supports to immobilize alcohol-containing small molecules, maleimide functionalized supports to immobilize thiol-containing small molecules. While the foregoing discussion has focused on immobilization via coupling the ligand to the support, other methods of immobilization can be used. For example, the ligands can be immobilized as a solution-phase chemical microarray (such as where the ligands are immobilized in wells or in which the ligands are immobilized as discrete droplets which are then contacted with the nucleic acid motif library using aerosol deposition technology) or as a dry chemical microarray.

As noted above, a plurality of ligands are immobilized on the support. In certain embodiments, at least 4 ligands are immobilized on the support. In certain embodiments, at least 10 ligands are immobilized on the support. In certain embodiments, at least 20 (e.g., at least 30, at least 40, at least 50, a least 60, at least 80, at least 100, at least 150, at least 200, etc.) ligands are immobilized on the support. Some or all of the ligands that are immobilized on the support can be structurally related, as in the case where some or all of the ligands that are immobilized on the support are congeners of one another.

The plurality of ligands are generally immobilized at the same loading, although this need not be the case. Suitable ligand loadings are from about 1 femtomole to about 100 nanomoles (such as from about 100 femtomoles to about 10 nanomoles and/or from about 1 picomole to about 1 nanomole) of ligand per discrete location.

In certain embodiments, at least one of the particular ligands is present at two or more different loadings, the two or more different loadings being immobilized at separate, discrete locations on the support. In certain embodiments, each of the particular ligands is present at two or more different loadings, the two or more different loadings being immobilized at separate, discrete locations on the support. In certain embodiments, at least one of the particular ligands is present at four or more different loadings, the four or more different loadings being immobilized at separate, discrete locations on the support. In certain embodiments, each of the particular ligands is present at four or more different loadings, the four or more different loadings being immobilized at separate, discrete locations on the support. Where two or more different loadings (e.g., 2, 3, 4, 5, 6, etc. different loadings) are employed for a particular ligand, the different loadings can be effected by serial dilution (e.g., as in the case where the first loading is x, the second loading is x/2, the third loading is x/4, the fourth loading is x/8, the fifth loading is x/16, etc.).

As noted above, the methods of the present invention further include contacting the plurality of immobilized ligands with a nucleic acid motif library under conditions effective for one or more members of the nucleic acid motif library to bind with the immobilized ligands.

In certain embodiments, the nucleic acid motif library is an RNA motif library. In certain embodiments, the nucleic acid motif library is a DNA motif library.

The nucleic acid motif library (e.g., RNA motif library, etc.) can include at least 4 members, such as in cases where the nucleic acid motif library includes at least 10 members, at least 20 members, at least 40 members, at least 60 members, at least 80 members, at least 100 members, at least 200 members least 500 members, at least 1000 members, at least 2000 members, at least 3000 members, at least 4000 members, etc. In certain embodiments, the nucleic acid motif library will contain members that differ from one another in the identity of the bases (i) in the nucleic acid motif and/or (ii) in the region near the nucleic acid motif (e.g., adjacent to the nucleic acid motif).

Illustratively, in certain embodiments, the method of the present invention is being used to identify an RNA motif which interacts with a ligand, and an RNA motif library is employed. For example, the RNA motif library can be an RNA internal loop library whose members differ from one another (i) in the identity of the bases in the RNA internal loop and/or (ii) in the identity of the base pairs adjacent to the RNA internal loop (the so-called loop closing base pairs). The RNA motif library can be, for example, a symmetric internal loop library, an asymmetric internal loop library, a 1×1 internal loop library, a 1×2 internal loop library, a 1×3 internal loop library, a 2×2 internal loop library, a 2×3 internal loop library, a 2×4 internal loop library, a 3×3 internal loop library, a 3×4 internal loop library, a 4×4 internal loop library, a 4×5 internal loop library, a 5×5 internal loop library, a 1 base bulge library, a 2 base bulge library, a 3 base bulge library, a 4 base bulge library, a 5 base bulge library, a 4 base hairpin loop library, a 5 base hairpin loop library, a 6 base hairpin loop library, a 7 base hairpin loop library, an 8 base hairpin loop library, a 9 base hairpin loop library, a 10 base hairpin loop library, a multibranch loop library, a pseudoknot library, etc. Combinations of these and other RNA motif libraries can be used. For completeness, it may be desirable to employ an RNA motif library which includes all possible combinations of bases (e.g., an 3×3 internal loop library containing 1600 different 3×3 internal loops). The members of the RNA motif library can further include (i.e., in addition to the variable RNA motif region) RNA regions that do not vary from member to member (e.g., invariant stem regions, invariant hairpin loop regions, etc.). Suitable RNA motif libraries can be prepared by conventional transcription techniques (e.g., those employing T7 RNA polymerase, as described, for example, in Milligan et al., "Synthesis of Small RNAs Using T7 RNA Polymerase," *Methods Enzymol.*, 180:51-62 (1989), which is hereby incorporated by reference) from DNA templates, such as DNA templates that are commercially available from Integrated DNA Technologies (Coralville, Iowa)).

By way of further illustration, in certain embodiments, the method of the present invention is being used to identify a DNA motif which interacts with a ligand, and a DNA motif library is employed. For example, the DNA motif library can be a DNA internal loop library whose members differ from one another (i) in the identity of the bases in the DNA internal loop and/or (ii) in the identity of the base pairs adjacent to the DNA internal loop (the so-called loop closing base pairs). The DNA motif library can be, for example, a symmetric internal loop library, an asymmetric internal loop library, a bulge library, a hairpin loop library, etc. Combinations of these and other DNA motif libraries can be used. For completeness, it may be desirable to employ a DNA motif library which includes all possible combinations of bases. The members of the DNA motif library can further include (i.e., in addition to the variable DNA motif region) DNA regions that do not vary from member to member (e.g., invariant stem regions, invariant hairpin loop regions, etc.).

In certain embodiments, at least 4 ligands are immobilized on the support, and the nucleic acid motif library (e.g., the RNA motif library, the DNA motif library, etc.) includes at least 100 members. In certain embodiments, at least 10 ligands are immobilized on the support, and the nucleic acid motif library (e.g., the RNA motif library, the DNA motif library, etc.) includes at least 100 members. In certain embodiments, at least 10 ligands are immobilized on the support, and the nucleic acid motif library (e.g., the RNA motif library, the DNA motif library, etc.) includes at least 1000 members.

In certain embodiments, the ligand is a small molecule, the nucleic acid motif is a DNA motif, and the nucleic acid motif library is a DNA motif library. In certain embodiments, the ligand is a small molecule, the nucleic acid motif is a DNA motif, the nucleic acid motif library is a DNA motif library, at least 10 ligands are immobilized on the support, and the DNA motif library includes at least 100 members. In certain embodiments, the ligand is a small molecule, the nucleic acid motif is an RNA motif, and the nucleic acid motif library is an RNA motif library. In certain embodiments, the ligand is a small molecule, the nucleic acid motif is an RNA motif, the nucleic acid motif library is an RNA motif library, at least 10 ligands are immobilized on the support, and the RNA motif library includes at least 100 members.

The plurality of immobilized ligands can be contacted with the nucleic acid motif library (e.g., the RNA motif library, the DNA motif library, etc.) by a variety of methods. For example, the nucleic acid motif library can be dissolved or suspended in a suitable solvent, buffer, or buffer system, and the immobilized ligands can be pre-equilibrated with a suitable hybridization buffer. The nucleic acid motif library can then be applied to the immobilized ligands, for example, by distributing the nucleic acid motif library evenly over the array surface; and the immobilized ligands and nucleic acid motif library can be incubated with one another for a period of time and at a temperature effective for one or more members of the nucleic acid motif library to bind with the immobilized ligands, such as, for example, at from about 15° C. to about 35° C. (e.g., at from about 20° C. to about 30° C. and/or at about room temperature) for from about 5 minutes to about 2 hours (e.g., from about 15 minutes to about 1 hour and/or for about 30 minutes). Even distribution can be effected by placing an inert film (e.g., a piece of PARAFILM™) over the applied solution, and the film can be left in place during incubation.

As noted above, the methods of the present invention further include identifying the members of the nucleic acid motif library (e.g., the RNA motif library, the DNA motif library, etc.) that are bound to a particular immobilized ligand. This can be carried out by harvesting members of the nucleic acid motif library that are bound at the discrete location on the support corresponding to the particular immobilized ligand. Harvesting can be carried out by any suitable technique, such as by direct excision. The harvested members of the nucleic acid motif library can then be cloned, RT-PCR amplified, and sequenced, using conventional techniques, such as those described in the Examples section of the present application.

The methods of the present invention can include additional steps. For example, in certain embodiments, the method the present invention can further include incubating the plurality of immobilized ligands with one or more chase oligonucleotides. "Chase oligonucleotides", as used herein, are meant to include oligonucleotides that are designed to ensure that the ligand interacts with the nucleic acid motif (i.e., with the nucleic acid motif library's variable region) and not with those nucleic acid regions that do not vary from member to member (e.g., invariant stem regions, invariant hairpin loop regions, etc.). The design of such stem chase and hairpin oligonucleotides will depend on the sequences used in the nucleic acid regions that do not vary from member to member, for example, as described in the Examples section of the present application. "Chase oligonucleotides", as used herein, are also meant to include DNA chase oligonucleotides (i.e., oligonucleotides that are meant to ensure that the interactions are RNA specific). Example of suitable DNA chase oligonucleotides include duplex AT decamers, duplex CG decamers, and combinations thereof. In certain embodiments, the one or more chase oligonucleotides includes stem chase oligonucleotides. In certain embodiments, the one or more chase oligonucleotides includes hairpin chase oligonucleotides. In certain embodiments, the one or more chase oligonucleotides includes DNA chase oligonucleotides. Combinations of these and other chase oligonucleotides can be employed, for example as in the case where the one or more chase oligonucleotides includes stem chase oligonucleotides, hairpin chase oligonucleotides, and DNA chase oligonucleotides.

Incubation with the one or more chase oligonucleotides is carried out prior to the step identifying members of the nucleic acid motif library (e.g., the RNA motif library, the DNA motif library, etc.) that are bound to a particular immobilized ligand; and incubation with the one or more chase oligonucleotides can be carried out, for example, subsequent to and/or concurrently with the step of contacting the plurality of immobilized ligands with the nucleic acid motif library. Typically, the chase oligonucleotides are employed at a concentration substantially greater than that of the nucleic acid motif library, such as at a concentration that is at least 10 times (e.g., at least 20 times, at least 50 times, at least 100 times, at least 200 times, at least 500 times, at least 1000 times, about 1000 times, etc.) the concentration of the nucleic acid motif library.

Using the aforementioned methods of the present invention, ligands which interact with particular nucleic acid motifs (e.g., with particular RNA motifs, with particular DNA motifs, etc.) can be identified. Since the nucleic acid sequences of many biologically important nucleic acid molecules are known, one can readily ascertain which biologically important nucleic acid molecules have the particular nucleic acid motifs with which a particular ligand interacts. Accordingly, the present invention can be used to identify ligands that bind or otherwise interact with biologically important nucleic acid molecules. Such ligands can be used to target such biologically important nucleic acid molecules, for example, for diagnostic or therapeutic purposes. In certain embodiments, such ligands can contain or otherwise be coupled to a probe moiety (e.g., a flourescent moiety) for identifying the presence (or quantifying the amount) of a particular nucleic acid in a sample. In certain embodiments, such ligands can contain or otherwise be coupled to a moiety that affects a particular nucleic acid's function (e.g., by affecting the nucleic acid's structure, by cleaving the nucleic acid molecule, etc.) for use as a therapeutic agent.

Ligand-nucleic acid motif interactions (e.g., ligand-RNA motif interactions, ligand-DNA motif interactions, etc.) identified in accordance with the methods of the present invention can also be used to design new molecules which target such biologically important nucleic acid molecules. For example, if, upon examination of a biologically important RNA molecule, it is determined that the biologically important RNA molecule contains two RNA motifs (e.g. Motif A and Motif B) in close proximity to one another and if, using the methods of the present invention, Ligand X was found to bind with Motif A and Ligand Y was found to bind with Motif B, one can design a new molecule, X—Z—Y (where Z represents a linking moiety), for targeting the biologically important RNA molecule.

The information regarding ligand-nucleic acid motif interactions (e.g., ligand-RNA motif interactions, ligand-DNA motif interactions, etc.) derived using the methods of the present invention can be assembled into a database. Such databases can then be used in methods for selecting, from a plurality of candidate ligands, one or more ligands that have increased likelihood of binding to a nucleic acid molecule having a particular nucleic acid motif (e.g., an RNA molecule having a particular RNA motif, a DNA molecule having a particular DNA motif, etc.). Such methods can include providing a database which correlates various ligands' abilities to bind to the particular nucleic acid motif and various other nucleic acid motifs (for example, in accordance with the methods of the present invention); comparing the candidate ligands' ability to bind to the particular nucleic acid motif; and choosing one or more ligands based on their ability to bind to the particular nucleic acid motif.

In certain situations, it may be desirable to select ligands which bind to one nucleic acid molecule but which do not bind to another nucleic acid molecule (e.g., ligands which bind to one RNA molecule but which do not bind to another RNA molecule, ligands which bind to one DNA molecule but which do not bind to another DNA molecule, etc.). The aforementioned databases can be used to make such selections. For example, such databases can be used in methods for selecting, from a plurality of candidate ligands, one or more ligands that have increased likelihood of binding to a first nucleic acid molecule comprising a first particular nucleic acid motif and that have decreased likelihood of binding to a second nucleic acid molecule comprising a second particular nucleic acid motif. Such methods can include providing a database which correlates various ligands' abilities to bind to the first particular nucleic acid motif, to the second particular nucleic acid motif, and to various other nucleic acid motifs (for example, in accordance with the methods of the present invention); comparing the candidate ligands' ability to bind to the first particular nucleic acid motif and to the second particular nucleic acid motif; and choosing one or more ligands based on their ability to bind to the first particular nucleic acid motif and their inability to the second particular nucleic acid motif. The first particular nucleic acid motif can be an RNA motif, and the second particular nucleic acid motif can be a DNA motif; the first particular nucleic acid motif can be a DNA motif, and the second particular nucleic acid motif can be an RNA motif; both the first and second particular nucleic acid motifs can be RNA motifs; or both the first and second particular nucleic acid motifs can be DNA motifs.

The present invention also relates to a method for identifying a nucleic acid which interacts with a ligand. The method includes providing a plurality of ligands immobilized on a support, wherein each particular ligand is immobilized at a discrete location on the support; contacting the plurality of immobilized ligands with a nucleic acid library under conditions effective for one or more members of the nucleic acid library to bind with the immobilized ligands; and identifying members of the nucleic acid library that are bound to a particular immobilized ligand.

Suitable methods for providing a plurality of ligands immobilized on a support include those which have been disclosed hereinabove. For example, suitable ligands which can be used in connection with this aspect of the present invention include proteins, polypeptides, carbohydrates, and other non-nucleic acid biopolymers; whole cells; and small molecules, such as those discussed hereinabove.

Suitable methods for contacting the plurality of immobilized ligands with a nucleic acid library; suitable conditions effective for one or more members of the nucleic acid library to bind with the immobilized ligands; and suitable ways to identify members of the nucleic acid library that are bound to a particular immobilized ligand include those methods and conditions which were discussed hereinabove in the context of contacting the plurality of immobilized ligands with nucleic acid motif libraries and in the context of identifying member(s) of the nucleic acid motif library that are bound to a particular immobilized ligand.

The nucleic acid library (e.g., an RNA or DNA library) can include at least 4 members, such as in cases where the nucleic acid library includes at least 10 members, at least 20 members, at least 40 members, at least 60 members, at least 80 members, at least 100 members, at least 200 members least 500 members, at least 1000 members, at least 2000 members, at least 3000 members, at least 4000 members, etc. In certain embodiments, the nucleic acid library will contain members that differ from one another in the identities of the bases in a particular region of the nucleic acid molecule (e.g., in a region containing from about 10 to about 40 bases, such as in a region containing from about 10 to about 35 bases, from about 10 to about 30 bases, from about 10 to about 25 bases, from about 10 to about 20 bases, from about 10 to about 15 bases, from 10 to 15 bases, 10 bases, 11 bases, 12 bases, 13 bases 14 bases, etc.), the remainder of the nucleic acid molecule being the same or substantially the same amongst the members of the nucleic acid library. The variable region can, but need not, contain structural motif(s); and if the variable region does contain structural motif(s), the ligand-nucleic acid molecule binding can, but need not occur at or otherwise involve the bases in the structural motif(s). As indicated above, the members of the nucleic acid library can have invariant regions. In certain embodiments, the variable region contains more bases than the invariant region. In certain embodiments, the invariant region contains about 40 bases or fewer, such as about 30 bases or fewer, about 20 bases or fewer, 10 bases or fewer, between about 10 and about 40 bases, between about 10 and about 20 bases, etc. In certain embodiments, the nucleic acid library is an X-mer nucleic acid library, wherein X is from about 10 to about 40, such as from about 10 to about 35, from about 10 to about 30, from about 10 to about 25, from about 10 to about 20, from about 10 to about 15, from 10 to 15, 10, 11, 12, 13, 14, etc.).

Illustratively, in certain embodiments, the method of the present invention is being used to identify an RNA which interacts with a ligand, and an RNA library is employed. For example, the RNA library can be a 10-mer to 40-mer RNA library, such as a 10-mer to 15-mer RNA library. By way of further illustration, in certain embodiments, the method of the present invention is being used to identify a DNA which interacts with a ligand, and a DNA library is employed. For example, the DNA library can be a 10-mer to 40-mer RNA library, such as a 10-mer to 15-mer DNA library.

For completeness, it may be desirable to employ a nucleic acid library (e.g., a RNA library or a DNA library) which includes all possible combinations of bases in the variable region.

In certain embodiments, at least 4 ligands are immobilized on the support, and the nucleic acid library (e.g., the RNA library, the DNA library, etc.) includes at least 100 members. In certain embodiments, at least 10 ligands are immobilized on the support, and the nucleic acid library (e.g., the RNA motif library, the DNA library, etc.) includes at least 100 members. In certain embodiments, at least 10 ligands are immobilized on the support, and the nucleic acid library (e.g., the RNA library, the DNA library, etc.) includes at least 1000 members.

Using the method of the present invention, nucleic acid(s) which interacts with a ligand can be identified. The nucleic acids (e.g., the RNA, the DNA, etc.) thus identified can be used to target the ligand. Illustratively, the nucleic acid can be coupled to a fluorescent or other probe and used to detect the presence (or quantify the amount or determine the location) of the ligand that may be present in a sample, such as a biological sample, a tissue sample, a blood sample, a urine sample, a cell sample, or in an organism.

The present invention is further illustrated by the following non-limiting examples.

EXAMPLES

Example 1—Using Selection to Identify and Chemical Microarray to Study the RNA Internal Loops Recognized by Kanamycin A: Overview In this Example 1 and in the following Examples 2-3, we describe our initial steps towards constructing a database of RNA-small molecule binding partners to aid rational design of compounds that target RNA. In order to do so, we have developed a selection-based approach that requires only a single round of selection to identify the RNA secondary structural elements (internal loops, hairpins, and bulges, for example) that bind small molecules. By screening RNA secondary structure libraries, we increase the chances of finding library members in a large biologically active RNA, such as rRNA. This is in contrast to Selective Exponential Enrichment (SELEX) experiments [53, 54] that have identified RNAs ranging from 17-mers to 30-mers that bind ligands with high affinity and specificity. Although the SELEX/aptamer approach finds high affinity RNA-ligand partners, it is unlikely to find these aptamers in a larger, biologically active RNA. In our initial study, we have screened a 4096 member RNA 3×3 internal loop library for binding to kanamycin A that is immobilized through the 6' amino group onto sepharose resin. We identified an ensemble of structures that binds the aminoglycoside and have scored their relative affinities using a microarray-based method. The highest affinity structures have 5'UU/3'UC 2×2 internal loops closed by A-U pairs.

Further details regarding the experiments described in this Example 1 and in the following Examples 2-3 can be found in Disney et al. "Using Selection to Identified and Chemical Microarray to Study the RNA Internal Loops Recognized by 6'-N-Acylated Kanamycin A," ChemBioChem, 8(6):649-656 (2007) and in the associated Supporting Infor-mation (available on the internet at www.wiley-vch.de/contents/ jc2268/2007/f600569 s.pdf) which are hereby incorporated by reference.

Example 2—Using Selection to Identify and Chemical Microarray to Study the RNA Internal Loops Recognized by Kanamycin A: Results and Discussion Selection of the RNA Internal Loops that Bind Kanamycin A.

Selection experiments were completed with kanamycin A (FIG. 1A, compound 1) immobilized onto sepharose resin and an RNA 3×3 internal loop library embedded in a hairpin cassette (R1, FIG. 2). This library was designed from a sequence used by others to identity RNA motifs that have interesting thermodynamic properties [34, 55]. Features of the library include an ultrastable GAAA (GNRA-type) hairpin [56] to facilitate proper folding and single stranded primer binding sites for amplification via RT-PCR. Kanamycin A was used in our initial study because it is a known RNA-binding ligand and it has been shown to bind non-canonically paired RNAs like those displayed in the random region of our library. Additionally, this ligand has been immobilized onto resin and used for selection experiments [54, 57].

A large excess of kanamycin A relative to the loading of succinimide esters on the sepharose was used to preferentially immobilize the ligand at the 6' $NH_2$ position, which is the most nucleophilic. It should be noted that when kanamycin A is acetylated at the 6' position, binding to an oligonucleotide mimic of the bacterial A-site is reduced several orders of magnitude relative to the parent aminoglycoside [47]. The reduction in binding affinity is due to elimination of important contacts that the 6' amino group forms with the A-site [11, 12, 58]. Therefore, we have challenged our system to find 6' acetylated kanamycin A-RNA secondary structural partners by using the modified aminoglycoside as bait to pull down members of the 3×3 internal loop library. The 6' $NH_2$ group has the potential to be used in future experiments as a reactive group for conjugation to link small molecule modules together to target a larger RNA.

Selections were completed by incubating a solution that contained 5' end $^{32}$P-labeled R1 in buffer with resin-immobilized kanamycin A. In addition to R1, a variety of other oligonucleotides were added to the incubation solution (R2-R4, D1, D2). We found that on average only 150 members (~4%) of the 4096-member 3×3 internal loop library bound to immobilized kanamycin A based on the percentage of the initial radioactivity that eluted with kanamycin A. This suggested that we did not have to increase the stringency of our selection by adding higher concentrations of chase oligonucleotides R2-R4, D1, and D2 and that the random regions in the library are being recognized. The small number may be due to the manner in which the ligand was immobilized onto the resin (impairs the 6' amino group from forming stabilizing contacts with RNA).

Selected RNAs were amplified via RT-PCR, cloned into a vector, and sequenced. The secondary structures of the selected RNAs were predicted by the RNA secondary structure prediction program RNAStructure [8]. A variety of structures were identified including six 1×1 internal loops half of which contain a C residue opposite a U residue, seven 2×2 loops with IL 1 and IL 2 having the same loop sequence but different orientation of a closing base pair, and five 3×3 loops (FIG. 3).

Studying the Binding of Selected RNA Internal Loops to Kanamycin A.

Figure 1B:
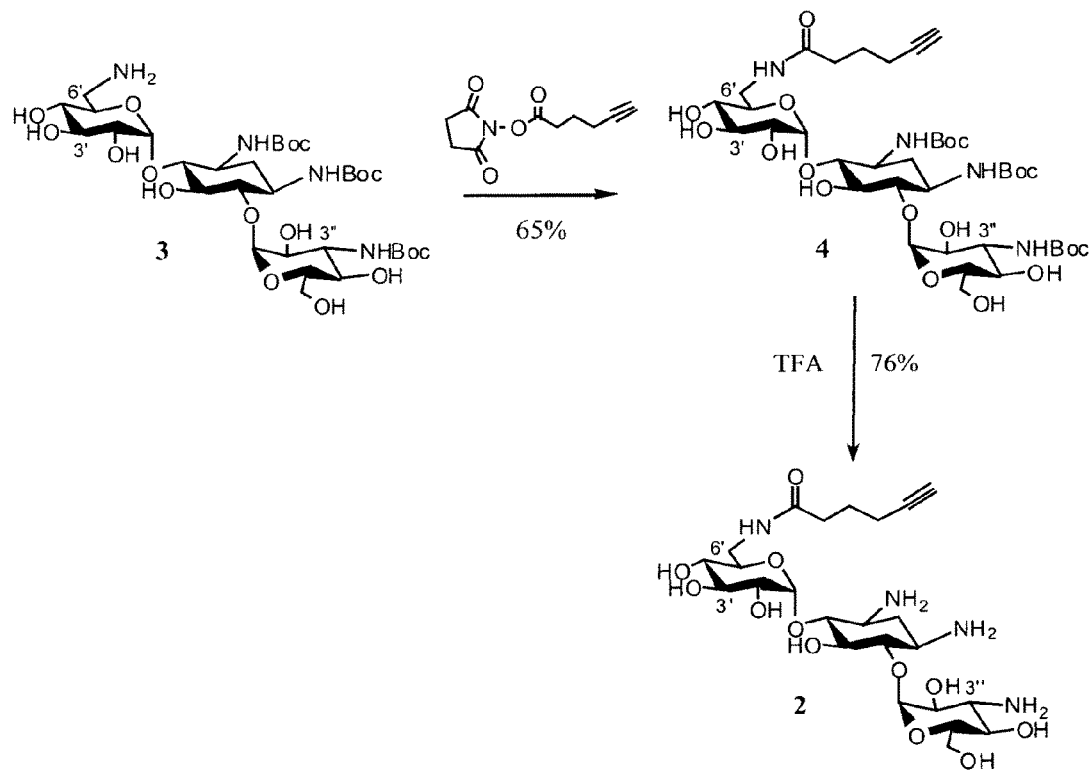
FIG. 1B is a reaction scheme showing the synthesis of 6'-N-5-hexynoate kanamycin A (2).

To score the binding affinity of each RNA internal loop, we developed an array-based method to determine relative affinities quickly. Microarrays have been used in a variety of experiments to probe the affinities of protein and RNA to small molecules in a rapid and highly parallel manner requiring minimal amounts of the analyte and ligand [28-29, 59-61]. To complete microarray-based affinity experiments with kanamycin A, we required a kanamycin A derivative that could be selectively immobilized onto an array surface. We envisioned that 6'-N-5-hexynoate kanamycin A (FIG. 1A, compound 2) would allow for defined immobilization via reaction of the alkyne handle with azide-displaying glass slides a using Huisgen dipolar cycloaddition reaction, or "click chemistry" [39]. The synthesis of 2 was completed as illustrated in the scheme presented in FIG. 1B. We used 1,3,3'-tri-N-(tert-butyl dicarbonyl) kanamycin A (3) [62] as the starting material in the synthesis since all amines except for the one at the 6' position are protected as acid-labile Boc groups. Compound 3 was reacted with N-succinimidyl-5-hexynoate to afford 4 in 65% yield. This compound was deprotected with trifluoracetic acid in 76% yield to afford the final product (2). A neamine derivative was also synthesized using the same synthetic sequence and was subsequently labeled with fluorescein by reaction with fluorescein isothiocyanate.

Figure 4A:
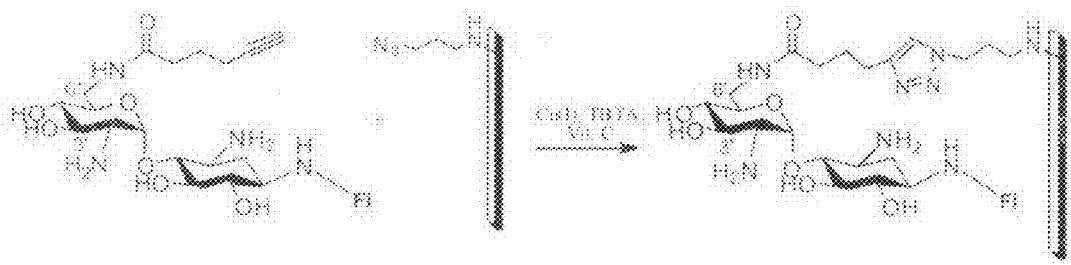
FIGS. 4A and 4B show the optimization of click chemistry conditions for immobilization of fluorescein labeled-6' hexynoate neamine onto azide displaying surfaces.
Figure 4B:
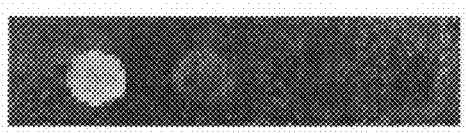

Fluorescein-labeled 6'-N-hexynoate neamine (neamine-Fl) was synthesized to test click chemistry immobilization conditions because the fluorescent signal allowed a direct readout of surface loading (FIGS. 4A and 4B). A solution of neamine-Fl was spotted onto azide-displaying agarose slides, and reactions were completed in the presence or absence of each reagent required for reaction. Loading of the labeled neamine-Fl onto the slide surface was only observed when all of the click chemistry reagents were added (sodium ascorbate, $CuSO_4$, and TBTA ligand). Signals that approach background were observed when any one of the reagents was removed from the spotting solution. These results indicate that 6' hexynoate neamine-Fl is reacting with the surface via triazole formation. We observe similar results when 6'-N-5-hexynoate kanamycin A is immobilized and then probed for binding to a radioactively labeled selected RNA.

Figure 5A:
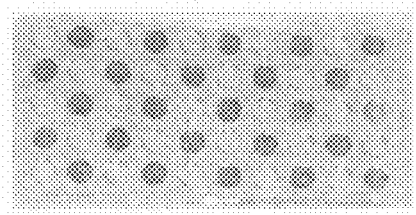
FIG. 5A is a photograph of a silicon gasket affixed to a microarray with half of the wells filled with a solution of dye.
Figure 5B:
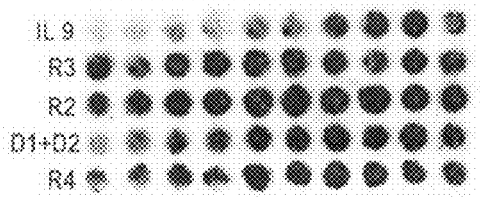
FIG. 5B is an autoradiogram of an array-based competitive binding assay completed with 5 different oligonucleotides.
Figure 5C:
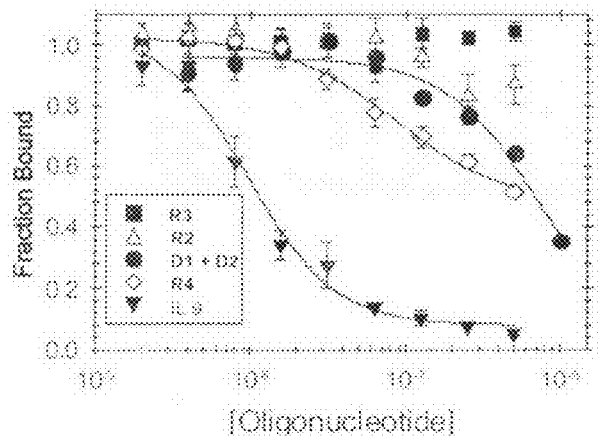
FIG. 5C is a graph showing the fit of the data for IL 9, the control oligonucleotides (R2, R3, and D1+D2), and the cassette (R4).

Typically microarray experiments can be used to probe the binding of a variety of small molecules to a single or a few analytes at once. In order to increase the number of conditions that can be probed on a single array, we affixed a silicon gasket that created 50 microwells on the surface of each chip (FIG. 5A). These microwells converted the array into a miniaturized 50-well plate that is easily functionalized to display kanamycin. Compound 2 was immobilized in each microwell at a constant concentration. Binding experiments were completed by delivering 10 μL of a solution containing serially diluted concentrations of the internal loop of interest and trace 5'end $^{32}P$ labeled IL 7 into each microwell. Dose response curves were constructed and fit to determine the concentration of competitor that inhibited 50% of the binding of the radioactively labeled RNA (FIG. 3, FIG. 5B, and FIG. 5C). FIG. 5B is a representative autoradiogram for binding selected RNAs relative to binding of control oligonucleotides R2, R3, D1 and D2, and R4, the cassette without an internal loop. All selected loops have at least a >20-fold lower $IC_{50}$ than tRNA or any of the control oligonucleotides used (FIG. 3). tRNA has approximately twice the number of nucleotides as our loop library, and its weak affinity for kanamycin A suggests that binding to the loops is not due to forming non-specific electrostatic contacts to the phosphodiester backbone. Moreover, each of the selected RNAs binds more tightly to kanamycin A than the entire library (R1) which has an $IC_{50}$ of 110 nM. These results suggest that our method selects for specific RNA internal loop-ligand interactions and eliminates the selection of weaker binders.

The two highest affinity sequences, IL 1 and IL 2, have $IC_{50}$'s of 2.2 and 3.3 nM, respectively. Both are 5'UU/3'UC 2×2 loops but they differ in the orientation of one of the closing A-U pairs. It is interesting to note that for tandem G•A pairs the orientation of the closing base pairs dramatically affects the structure of the internal loops formed. [45, 46] It appears that is not the case when a single pair in IL 1 and IL 2 is changed based on this data. The five highest affinity binders (IL 1-5) contain two U's in the same position on opposite sides of the loop (FIG. 3). IL 18 also displays this sequence pattern; however, the U's are flanked by purines. It is possible that their presence affects loop structure or dynamics and is the cause of decreased affinity. If one of the U's on opposite sides of the loop in IL 1 and IL 2 is replaced with a C and the closing base pair is changed from AU to GC, the resulting loop, IL 17, binds ~10-fold weaker. This suggests that the aminoglcoside is forming contacts with loop nucleotides and/or the closing base pair or that the structure of the loop is altered when the nucleotides are mutated.

The binding site of 2 was determined by enzymatic probing of IL 7 and R4 in the presence or absence of 2 with RNase A and S1 nuclease. Results show that only nucleotides in the loop and the surrounding base pairs in IL 7 are protected from cleavage. No nucleotides in the cassette R4 are protected (FIGS. 6A and 6B). These results coupled with the relative binding measurements further suggest that we have selected specific RNA internal loop-small molecule partners. We have also observed decreased modification by diethyl pyrocarbonate ("DEPC") of loop nucleotides in IL 1 and IL 16 when 2 is present. DEPC has been shown to modify U's at slightly basic pH [63, 64].

A variety of biologically important RNAs bind aminoglycosides including the A-site in bacterial ribosomes [65, 66], and TAR [67] and REV [68] RNAs from HIV. Aptamers to tobramycin and kanamycin have also been selected [54, 57]. Interestingly, the aptamers for kanamycin and tobramycin, [54, 57] TAR RNA, [67] and the A-site [11, 58, 65] all have unpaired U's in the sites that bind to the aminoglycoside. The consensus region in one tobramycin aptamer contains a ten nucleotide hairpin in which four of the hairpin nucleotides are U's [54]. In TAR RNA, two of the three nucleotides in the bulge that binds tobramycin are U's, and there is a 1×1 U•U internal loop in the A-site in bacterial ribosomes. Structural studies of aminoglycosides bound to the A-site show that the aminoglycoside forms direct contacts to the U•U pair (U1406•U1495) through the 2-deoxystreptamine ring common to all aminoglycosides [58]. Based on these studies it is clear that the aminoglycosides bind to a wide array of non-canonically paired RNA structures, with a preference for U. This may be due to the conformational flexibility of aminoglycosides, allowing them to fit into a variety of RNA folds [69]. Taken together with our study, these collective data suggest that aminoglycosides prefer RNAs that have non-canonically paired or unpaired U's. We have identified a consensus 2×2 RNA internal loop sequence displaying unpaired or non-canonically paired U's that binds 6'acetylated kanamycin A. These results further our understanding of the RNA internal loops bound by ligands and may also give insight into off-target effects when aminoglycosides bind to bystander RNAs. This information could aid design of less toxic aminoglycosides.

In this Example 2 and in related Examples 1 and 3, we have described the development of two methods to quickly identify RNA-small molecule partners and to quickly score their relative affinities. Results from this study represents out first entry into constructing a database of small molecule-RNA secondary structural motif interactions. This rational approach has the potential to allow more efficient identification of lead small molecules that modulate RNA structure and function.

Example 3—Using Selection to Identify and Chemical Microarray to Study the RNA Internal Loops Recognized by Kanamycin A: Materials and Methods This Example 3 describes the materials and methods that were used in carrying out the experiments described in Example 2.

Selection and Nucleic Acid Synthesis. General Methods.

Nanopure water was used in all experiments. All solutions for buffers were prepared with DEPC-water to insure the absence of nucleases. All DNA oligonucleotides were purchased from Integrated DNA Technologies ("IDT") Coralville, Iowa) and were purified by denaturing 17% PAGE. DNAs were visualized by UV shadowing, and the products were extracted from the gel slice by tumbling overnight in sterile 0.3 M NaCl at 4° C. tRNA XSA from Baker's yeast used in the microarray binding experiments was purchased from Sigma-Aldrich. N-hydroxyl succinimide-activated sepharose was purchased from Amersham. Reverse transcriptase was obtained from Life Sciences, Inc. (St. Petersburg, Fla.). Oligonucleotide extinction coefficients were determined on the HYTHER™ server available from the SantaLucia laboratory (HYTHER™ version 1.0, Wayne State University) [70, 71]. Parameters therein are based on extinction coefficients of nearest neighbors in RNA [72].

RNA Oligonucleotide Synthesis.

The oligonucleotides R1 and R4 and the two oligonucleotides that comprise the duplex R2 were synthesized by run off transcription of synthetic DNA templates using T7 RNA polymerase [50]. Oligonucleotide R3 was purchased from IDT (Coralville, Iowa). Purity of all oligonucleotides was determined to be >90% from analytical kinase experiments completed as previously described [51]. Plasmids encoding the selected sequences were amplified via PCR with a primer that contained a recognition site for T7 RNA polymerase. (See "Selection of RNA Internal Loops", infra, for complete details.) The products of the PCR reaction were then used directly for transcription using the same methods described above. Reactions were purified on a denaturing 17% polyacrylamide gel. Products were visualized and extracted from the gel as described in "General Methods", supra.

Attachment of Aminoglycosides to N-Hydroxyl Succinimde-Activated Sepharose.

A 2.4 mL suspension of resin in isopropanol (1.2 mL of resin, loading 18 µmol/mL) was placed into a BioRad polyprep chromatography column and washed twice with 10 mL of $H_2O$. To the washed resin was added 50 mg (105 µmol) of kanamycin A in 5 mL of $Na_2CO_3$ buffer, pH 9.0, and the resin was tumbled overnight at 4° C. After incubation, the resin was washed 2× with 10 mL of buffer, and the remaining succinimide esters were quenched with 5 mL of 10 mM ethanolamine in 5% $Na_2CO_3$ (1 h at room temperature ("RT") with tumbling) The resin was washed with water and then sequentially washed with 10 mL of 10 mM $NH_4OAc$, pH 4.5, and 10 mL of 10 mM Tris.HCl, pH 8.0. These steps were repeated 3×, and the resin was stored in 10 mM Tris.HCl, pH 8.0 at 4° C. Excess aminoglycoside relative to succinimide esters loaded on the resin and incubation at 4° C. were used for conjugation to allow reaction to occur preferentially at the 6' amino position of kanamycin A. Previous experiments have shown that this position is the most reactive when aminoglycosides are conjugated to dyes that contain succinimide esters and to resin [54, 60, 73].

Selection of RNA Internal Loops that Recognize Kanamycin A.

Each of the oligonucleotides was refolded separately in Hybridization Buffer ("HB") containing 8 mM $Na_2HPO_{31}$ pH 7.0, 1 mM EDTA, and 185 mM NaCl by heating for 5 min at 65° C. and then cooling to RT on the benchtop. Oligonucleotides were then transferred to 4° C. and mixed together. Before the oligonucleotides were hybridized with the resin, 200 µg of BSA was added to the samples. Each selection experiment was completed with 10 picomoles of 5'-end labeled R1 and 20-fold higher concentration of each control oligonucleotide (R2-R4, D1, D2) over the concentration of R1.

A 100 µL aliquot of resin slurry (10 µL of resin) was placed into a 2.5 mL BioRad column and washed 3× with 1 mL of 4° C. HB. The resin was then washed as follows: (1) 2.5 mL of HB containing 10 pmoles of R1; (2) 5 mL of HB; (3) 2.5 mL of HB containing 200 pmoles of all RNA chase oligonucleotides (R2-R4); (4) 2.5 mL of HB containing 200 pmoles of all DNA chase oligonucleotides (D1, D2); (5) 2×5 mL of HB. At this stage, liquid scintillation counting was used to ensure that only background radioactivity was being eluted from the column. Bound RNAs were eluted by delivering a 2 mL solution of HB containing 1 mM of the immobilized ligand. Scintillation counting of the elution showed that only a small percentage of R1 (~4%) bound to the immobilized ligand.

The eluate was concentrated to 500 µL with 2-butanol and ethanol precipitated with 100 µg of glycogen as a carrier. The sample was resuspended in 100 µL of $H_2O$ and treated with RQ DNase I (RNase-free, Promega) by incubation at 37° C. for 3 h. An equal volume of stop buffer was added to the reaction, and the sample was incubated at 65° C. for 10 min to inactivate the DNase. After phenol:chloroform extraction and ethanol precipitation, the sample was used as a template in RT-PCR reactions.

RT-PCR reactions were completed as described previously [34, 55, 74]. Control experiments were run to ensure that there was no contamination in the samples, including no template and template without RT controls. Primers used for RT-PCR experiments are: PCR primer, 5' GGCCGAATTCTAATACGACTCACTATAGGGAGAGGGTTTAAT (SEQ ID NO:1), containing a T7 promoter for transcription with RNA polymerase; RT primer, 5' CCTTGCTCCAAT (SEQ ID NO:2). RT reactions were completed by annealing 20 µL of the isolated RNA solution and 2 µL of a 100 µM solution of RT primer at 70° C. for 10 min followed by incubation on ice for 10 min. Then, 1.6 µL of 25 mM dNTPs, 0.8 µL of 10 mg/mL BSA, 4 µL of 10×RT buffer (supplied by the manufacturer), and 0.1 µL of RT or $H_2O$ for no RT controls were added. The reaction was allowed to proceed for 1 h at 60° C. at which point the reaction was quenched by heating at 95° C. for 3 min. PCR amplification was completed by adding 4 µL of 100 µM PCR primer, 2 µL of 100 µM RT primer, 0.6 µL of 250 mM $MgCl_2$, 0.2 µL of Taq polymerase, 13 µL of $H_2O$, and 6 µL of 10×PCR buffer. Twenty cycles of PCR were completed at 95° C. for 1 min/72° C. for 1 min. Reactions were analyzed by running an aliquot on a denaturing 17% polyacrylamide gel stained with SYBR gold or ethidium bromide. Only experiments in which the negative controls contained no product were carried on towards cloning.

RT-PCR products were then digested with BamHI and EcoRI and were ligated into a pUC19 vector that was digested with the same enzymes [34, 55, 74]. The plasmids were transformed into DH5α competent *Escherichia coli* and plated on LB plates containing ampicillin, X-gal, and IPTG. White colonies were used to inoculate 2.5 mL Luria Bertani broth (LB) cultures containing ampicillin and were grown overnight at 37° C. Plasmids were isolated from bacteria using an Eppendorf fast plasmid mini kit. Sequencing reactions were completed by the Roswell Park Cancer Institute's Biopolymer lab.

Microarray-Based Experiments.

Preparation of azide-functionalized glass slides. Aminosilane slides (Sigma) were coated with ca. 2 mL of a 1% melted agarose solution [31]. Slides were placed on the bench and allowed to dry to a clear film. The agarose-coated slides were submerged in a 20 mM $NaIO_4$ aqueous solution for 30 min [31] followed by extensive washing in water (3×30 min with frequent water changes). Slides were then submerged in 10% aqueous ethylene glycol for 1.5 h and were washed with water as described above. To display azides, slides were reacted with 20 mM 3-azidopropylamine in 0.1 M $NaHCO_3$ overnight. The following morning, slides were quenched by incubation for 3 min in $NaCNBH_3$ solution (100 mg in 10 mL ethanol+40 mL PBS). Slides were washed with water as described above and left to dry to a clear film on the benchtop.

Click Reactions on the Slide Surface.

Click reaction conditions on the slide surface were optimized using a FITC-neamine substrate by varying the concentrations of $CuSO_4$, TBTA, and sodium ascorbate or TCEP in 1× phosphate buffer containing 10% glycerol. Solutions were incubated on the slide surface for 2 h at RT, and then washed with 1×SDS for 15 min and with water for 15 min. The slides were dried in a stream of air and imaged using a Kodak Gel Imaging System equipped with a 535 nm filter. The optimal reaction conditions found were 1 mM $CuSO_4$, 100 µM TBTA, and 5 mM sodium ascorbate. Reactions are specific because no reaction occurs when $Cu^{2+}$ or TBTA are removed from the reaction, and only slight signal is observed in the absence of sodium ascorbate (FIG. 4B). These conditions were used to immobilize 2.

Determination of $IC_{50}$'s and Relative Binding Affinities.

In order to determine which concentration of 2 was optimal for competitive binding assays, serially diluted 2 was applied to the chip surface and allowed to react for 2 h at RT inside the microwell of a silicon gasket (GRACE Biolabs, CWCS 50R-1.0, C-24780) (FIG. 5A). Each of the wells was washed twice with water, and the slide was dried in air. The 5' end $^{32}P$ radiolabeled IL 7 was annealed in 1×HB+40 µg/mL of BSA at 60° C. for 5 min and allowed to slow cool on the benchtop for 10 min. It is important to note that the hybridization buffer contains 1 mM EDTA, or 50 equivalents compared to the amount of $Cu^{2+}$ used for the click reaction. EDTA was included to ensure that $Cu^{2+}$ does not bind to the aminoglycoside and cleave the RNA phosphodiester backbone [75]. The annealed RNA oligonucleotide was hybridized with the chip surface for 30 min at RT. Slides were washed twice for 2 min with 1×HB+40 µg of BSA. Slides were dried in a stream of air and imaged using a BioRad FX Imager. This direct binding measurement showed that delivering 400 nL of a 2.5 mM solution of 2 to the array was sufficient to observe binding to radiolabeled IL 7.

$IC_{50}$'s were determined by incubating serially diluted competitor RNA and trace radiolabeled IL 7 in microwells formed using a silicon gasket. Briefly, the internal loop for which the $IC_{50}$ was determined was annealed in 1×HB+40 µg/mL BSA as described above. IL 7, which was used to optimize the concentration of 2 in the spotting solution, was annealed separately in the same manner. After slow cooling on the benchtop for 10 min, the radiolabeled internal loop was added to serially diluted competitor RNA, and the sample applied to a microwell. The solution was allowed to equilibrate with the surface for 30 min at RT after which the slide was washed twice with 1×HB+40 µg/mL BSA. After drying in a stream of air, the slides were exposed to a phosphorimager plate and imaged using a Bio-Rad FX Imager. The data were quantified using Bio-Rad's QuantiyOne software, and the $IC_{50}$'s were determined using SigmaPlot's four-parameter logistical curve fit.

Enzymatic Probing of RNA. Hydrolysis and Nuclease T1 Ladders.

Hydrolysis ladders were generated by incubating 5' end $^{32}P$ radiolabeled RNA oligonucleotides in 150 mM $NaHCO_3$, pH 10 and 1 mM EDTA for 4 min at 95° C. Nuclease T1 cleaves after single stranded guanosine nucleotides. A T1 Ladder was generated under denaturing conditions by incubating radiolabeled RNA oligonucleotides in 20 mM sodium citrate, pH 5, 7 M urea, 1 mM EDTA, and 0.25 u of T1 at 55° C. for 5 min. Both reactions were quenched by adding equal volumes of stop buffer (1×TBE, 8 M urea, and 1 mM EDTA).

RNase A and S1 Nuclease Mapping.

The binding site(s) of 2 was determined using a nuclease protection assay. For RNase A mapping experiments, radiolabeled oligonucleotide was annealed as described above. After slow cooling, serially diluted concentrations of 2 were added, and the resulting solution was allowed to equilibrate for 30 min at RT. Approximately 6 µunits of RNase A were added, and the reaction was allowed to proceed for 10 min. The reaction was quenched by addition of an equal volume of stop buffer, and the products were separated on a denaturing 17% polyacrylamide gel.

For S1 nuclease mapping experiments, the radiolabeled oligonucleotide was annealed as described except the buffer used was 50 mM sodium acetate (pH 4.5), 280 mM NaCl, and 4.5 mM $ZnSO_4$. The solution was allowed to equilibrate for 30 min at RT after the addition of serially diluted concentrations of 2, and then 10 units of S1 were added. The reaction was quenched after 10 min at RT, and the products were separated on a denaturing 17% polyacrylamide gel.

Figure 7:
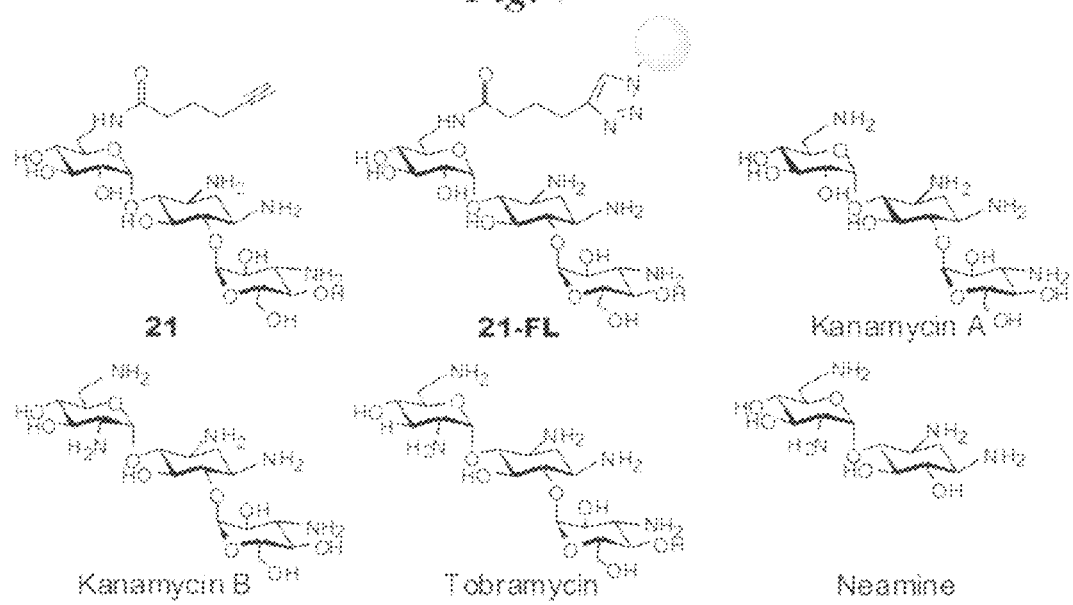
FIG. 7 is a drawing showing the structures of various aminoglycosides and derivatives thereof that can be used as small molecule ligands in the methods of the present invention. Compound 21 is 6'-N-5-hexynoate kanamycin A and was used in selection experiments described herein. Compound 21-FL is 21 conjugated to fluorescein via a Huisgen dipolar cycloaddition reaction; the dye is indicated with the ball. 21-FL was used in fluorescence assays to determine dissociation constants. Kanamycin A, kanamycin B, tobramycin, and neamine were used in competitive binding experiments to determine aminoglycoside preferences for a selected internal loop.

Example 4—A Small Molecule Microarray Platform to Select RNA Internal Loop-Ligand Interactions: Overview In this Example 4 and in the following Examples 5-6, we describe a microarray platform to complete nucleic acid selections that combines the advantages of selection methods and small molecule microarrays. Our basic approach is to immobilize ligands onto an agarose microarray surface and screen the ligands for binding to an RNA motif library. The RNAs that bind members of the ligand library are harvested directly from the array surface by gel excision, cloned, and identified via sequencing. This approach was applied toward identifying the RNA internal loops that bound 6'-N-5-hexynoate kanamycin A (21, FIG. 7). Results show that 21 binds to internal loops that can form potential CA pairs. All selected RNA internal loops bind 21 with $K_d$ values ≤22 nM.

Further details regarding the experiments described in this Example 4 and in the following Examples 5-6 can be found in Childs-Disney et al., "A Small Molecule Microarray Platform to Select RNA Internal Loop-Ligand Interactions.," *ACS Chem. Biol.*, 2(11):745-754 (2007) and in the associated Supporting Information (available on the internet at http://pubs.acs.org/subscribe/journals/acbcct/suppinfo/cb700174r/cb700174r-File003.pdf), which are hereby incorporated by reference.

Figure 8A:
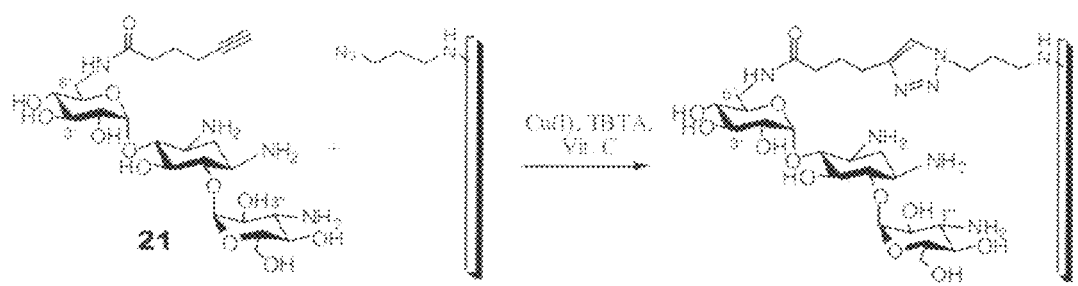
FIG. 8A is a schematic of the immobilization of 21 onto azide-functionalized agarose slides via a Huisgen dipolar cycloaddition reaction.
Figure 8B:
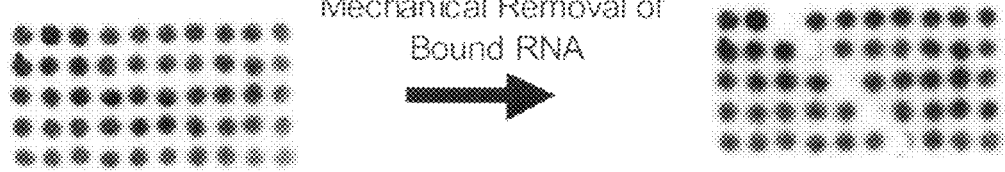
FIG. 8B are representative autoradiograms of (left) an array hybridized with radioactively labeled 22 and (right) an array after excision of bound RNAs. Bound RNAs can be amplified by RT-PCR, cloned, and sequenced.

Example 5—A Small Molecule Microarray Platform to Select RNA Internal Loop-Ligand Interactions: Results and Discussion The Microarray Platform and the RNA Library.
Optimization of the merging of nucleic acid selections and small molecule microarrays required a unique microarray surface that is robust enough for ligand screening and allows bound RNAs to be harvested directly from the array surface. We found that the optimal surface for this application is an agarose-coated microarray [31-33]. Agarose provides a three-dimensional surface for high ligand loading and a versatile surface to accommodate a variety of immobilization chemistries, and bound RNAs can be harvested from the array surface by simple excision of the agarose from ligand-functionalized positions (FIG. 8B).

The RNA library (22) that was screened for binding 21 has six randomized positions displayed in a 3×3 nucleotide internal loop pattern (FIG. 9) (34). By focusing on selecting RNAs from this library, we focus selections only on small RNA motifs that are likely to be found as constituents of larger RNAs. This is in contrast to SELEX, which uses libraries with ~15 randomized nucleotides. These 15-mers are very difficult to find in biological RNAs; however, in rare occasions SELEX has proven successful in RNA-targeting endeavors [35, 36]. Library 22 has 4096 members that can form a variety of internal loops and also base paired regions. Specifically, 2 contains 1600 different 3×3 internal loops, 1200 different 2×2 loops, 1080 different 1×1 loops, and 216 different base paired regions. (These values were calculated by assuming that a GU pair is a standard RNA pair and that two 1×1 internal loops cannot be separated by a base pair; these structures are counted as 3×3 loops.)

Development of the Microarray Selection Method.

Figure 10A:
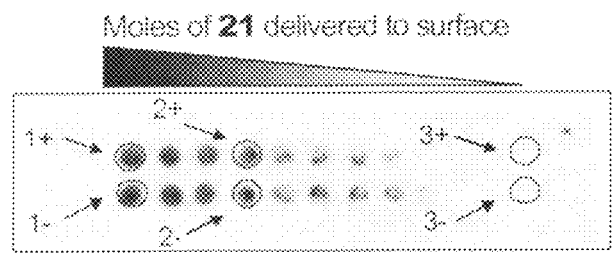
FIG. 10A is an image of an array after hybridization with 10 nM of 5' end $^{32}$P-labeled 22 and 10,000 nM each of chase oligonucleotides 23-26.
Figure 10B:
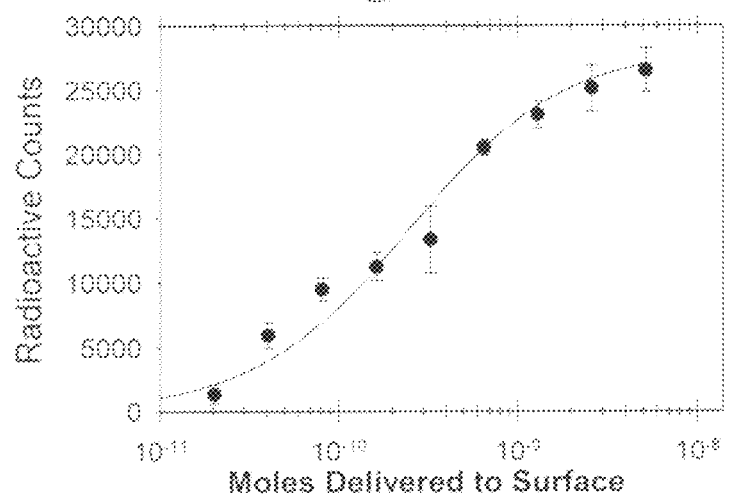
FIG. 10B is a dose-response curve for binding to 21 in the presence of chase oligonucleotides 23-26 on the array. The extracted positions are circled.
Figure 10C:
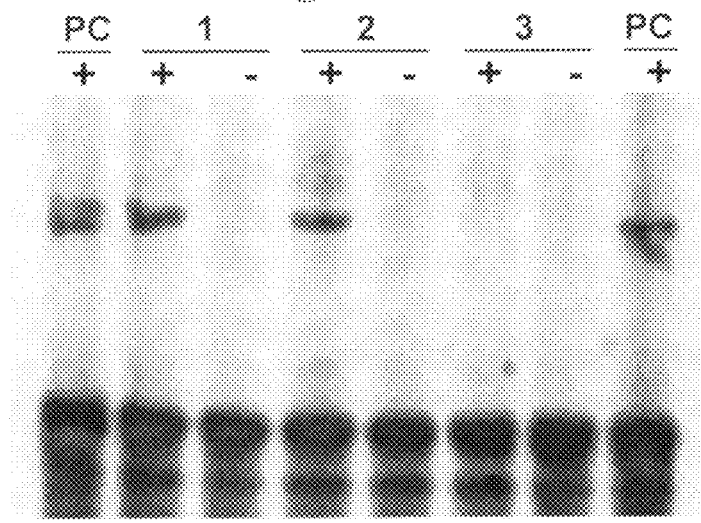
FIG. 10C shows the results from RT-PCR amplification of RNA harvested from the array. The plus sign ("+") indicates RT was added to the RT-PCR reaction. The minus sign ("−") indicates RT was not added to the RT-PCR reaction. "PC" refers to a positive control for RT-PCR. The affinities of 21 for RNAs from position 1+ and 2+ are 65 nM and 11 nM, respectively.

An array containing 50 ligand-functionalized spots was constructed by immobilizing 21 onto azide-functionalized surfaces via a Huisgen dipolar cycloaddition reaction [37, 38]. The array was then probed for binding to 5' end $^{32}$P-labeled 22. All positions where 21 was immobilized bound members of 22 with similar intensities (FIG. 8B). A diagonal of spots was excised from the array to assess if bound RNAs can be harvested precisely without affecting adjacent spots. Images of the array taken before and after excision show that RNA was harvested only from the desired positions and that signals in the surrounding spots were unaffected (FIG. 8B); thus there is no cross-contamination between spots. Harvested RNA is suitable for amplification by reverse transcriptase polymerase chain reaction (RT-PCR), cloning, and sequencing to identify the selected library members (FIG. 10A). Next, we immobilized serially diluted concentrations of 21 onto azide-agarose and incubated the slide with 5' end $^{32}$P-labeled 22 and unlabeled chase oligonucleotides (FIG. 9). Chase oligonucleotides included a mimic of the stem (23) and hairpin (24) in 22 and DNAs that formed d(GC) (25) and d(AT) (26) Watson-Crick pairs. This combination was used to ensure that only internal loop-small molecule interactions were probed in the selection and that interactions were RNA-specific. For the experiments in FIGS. 10A-10C, chase oligonucleotides were added in 1000-fold excess over 22 and in excess over the amount of ligand delivered to the array surface. Under these conditions, concentration-dependent binding is observed to 22 with signals that are well above background (FIGS. 10A-10B). Six samples were collected from the surface where different amounts of 21 were immobilized (FIG. 10A) and amplified by RT-PCR (FIG. 10C). RT-PCR product was only observed when samples were taken from positions functionalized with 21 and when RT was added to the RT-PCR reactions. No RT-PCR product was observed when samples were taken from a position where 21 was not delivered or when RT was not added to the RT-PCR reaction, provided ≤30 cycles of PCR were used.

One advantage of screening different concentrations or loadings of ligands is higher affinity RNA motif-ligand interactions should be identified at lower ligand loadings. To determine if this is indeed the case, we studied the binding of the pools of RNAs harvested from 1+ (higher ligand loading) and 2+ (lower ligand loading) by using a fluorescence-based assay. Compound 21 was fluorescently labeled (21-FL, FIG. 7) by reacting Boc-protected 21 with propargylamine using the Huisgen dipolar cycloaddition reaction used to anchor 21 onto the array surface. The product of this reaction was reacted with fluorescein isothiocyanate to yield 21-FL. Dissociation constants for the binding of 21-FL to the library of RNAs was determined because the fluorescence emission of 21-FL decreased as a function of RNA concentration. The resulting curves were used to determine dissociation constants. Results show that $K_d$ values for 1+ and 2+ are 65 nM and 11 nM, respectively (FIG. 10C). Evidently, RNAs harvested at a lower ligand loading have higher affinities for 21.

Since RNAs harvested from the surface can be RT-PCR amplified and subsequently used as templates for runoff transcription, multiple rounds of selection can be completed if desired. The ability to complete selections at different ligand loadings on the same surface demonstrates that this platform can be used to complete multiple selections in parallel on a single array.

Figure 11A:
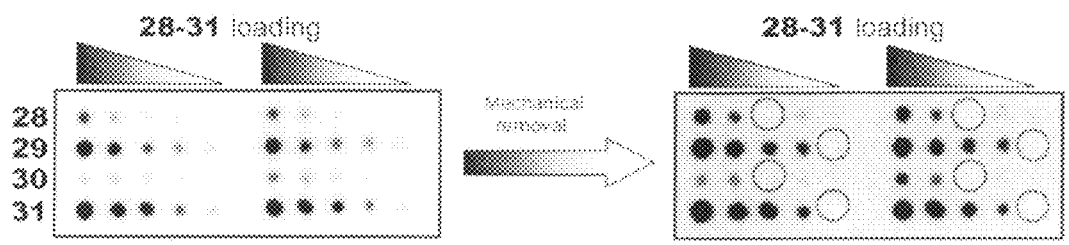
FIGS. 11A-11C relates to a two-dimensional combinatorial screen of an array-immobilized aminoglycoside library for binding to members of 22.
Figure 11B:
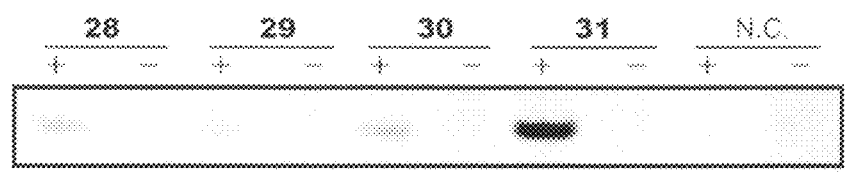
Figure 11C:
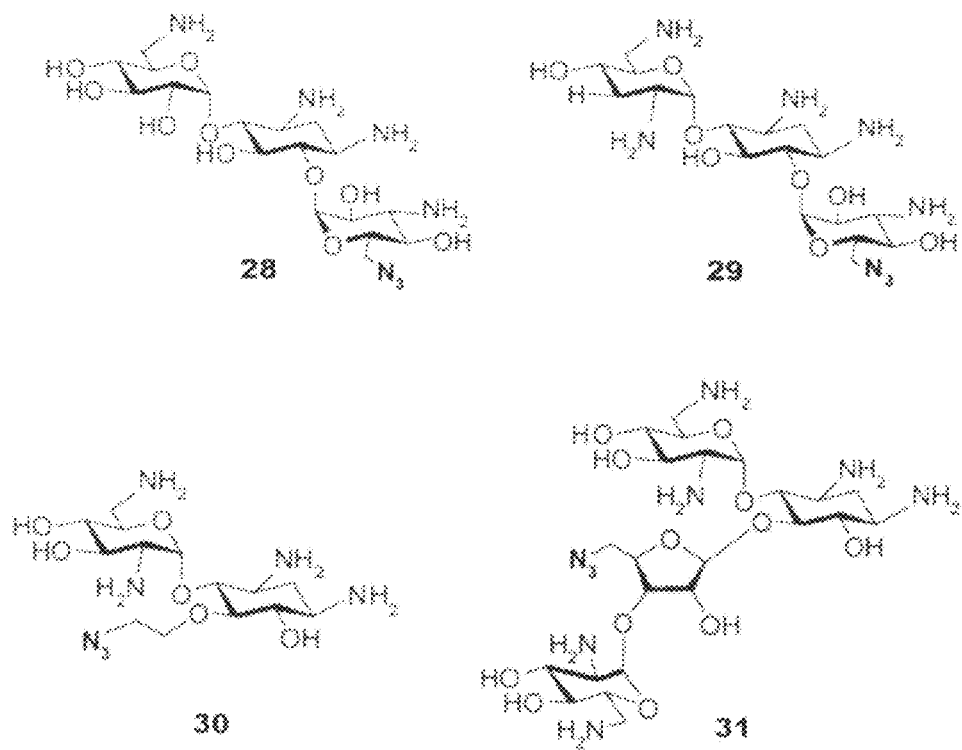

To further illustrate that multiple selections can be completed on a single agarose array platform, we immobilized a four-member azido-aminoglycoside library (FIG. 11C, 28-31) onto alkyne-functionalized agarose [37, 39] and selected members of 22 that they bound. Each library member was immobilized at five different loadings and probed for binding 22 in the presence of 23-26. Members of 22 bound to these structures with signals that depend on both the aminoglycoside loading and identity. Bound RNAs at the indicated positions in FIG. 11A were harvested and were cleanly RT-PCR amplified over positions excised from where aminoglycoside was not delivered to the array surface (background) (N.C., FIG. 11B). When only the number of aminoglycosides are considered for binding 22, 4×4096 or 16,382, interactions were probed in duplicate; however if the number of aminoglycosides (four) and their loadings (five each) are considered, 4×5×4096, or 81,920, interactions were probed in duplicate.

Analysis of the Sequences of the Selected Structures that Bind 21.

Selected higher affinity RNAs from 2+ (FIG. 10C) were cloned and sequenced, and their secondary structures predicted by free energy minimization using the RNASTRUCTURE program (FIG. 12) [8]. Interestingly, many of the selected loops share sequence similarities. There is a clear preference for loops with adenine across from cytosine. (We state adenine across from a cytosine rather than A-C pair to denote that we do not know if these bases are indeed paired.) Of the 16 loops identified from the selection, (62.5%) contain at least one adenine across from a cytosine, in contrast to only 33% of all library members (two-tailed p-value=0.0124). For each internal loop class, the selection of at least one adenine across from an cytosine is above the rate if the selection were random: 60% of 1×1 nucleotide internal loops, 66% of 2×2 nucleotide internal loops, and 60% of 3×3 nucleotide internal loops. (Of the 1080 1×1 nucleotide internal loops in 22, 20% have an adenosine across from a cytosine; 36% of 2×2 nucleotide internal loops contain at least one adenosine across from a cytosine; 44% of 3×3 nucleotide internal loops contain at least one adenosine across from a cytosine. For the entire library, 22, 33% of the loops contain at least one adenosine across from a cytosine.

Other sequence preferences are also observed. For the 2×2 nucleotide loops, the predicted lowest free energy structures show preferences for pyrimidines neighbored by adenine across from cytosine (two-tailed p-value=0.0093). The preference for pyrimidines in 2×2 nucleotide internal loops was also observed in our resin-based selection, as described in Examples 1-3, supra. Interestingly, many of the 1×1 and 2×2 nucleotide internal loops are closed by G•U base pairs. The predicted lowest free energy structures of the 3×3 nucleotide loops also show a preference for purines (two-tailed p-value=0.0309). In fact, for the two 2×2 and two 3×3 nucleotide internal loops that do not contain an adenine across from a cytosine, three of them contain either a guanine across from a guanine or a cytosine across from a cytosine, which are both observed in the 1×1 loops. This may suggest that the motifs displayed in the 1×1 nucleotide loops are also displayed in the 3×3 nucleotide loops. The one 2×2 nucleotide loop that does fit either criterion (IL 28) has tandem guanines across from adenines, which are displayed in many of the selected 3×3 nucleotide loops (IL 32, IL 33, and IL 35). The exact pairings that give rise to these structural features will have to be determined through structural biology investigations, but it will be interesting to see if these sequences display a similar RNA structural scaffold to bind 21.

Measuring the Affinities of Selected Structures to 21-FL.

The affinity of each loop was determined using the fluorescence assay described above. Each selected internal loop binds to 21 with a similar affinity, all with $K_d$ values ≤22 nM (FIG. 12). The range of dissociation constants (5-22 nM) corresponds well to the dissociation constant determined for the pool of RNAs harvested from position 2+ (11 nM). In contrast, 21-FL binds more weakly to the chase oligonucleotides and the library. The fluorescence intensity of 21-FL did not change in the presence of 23, 24, and 25+26 at concentrations up to 5 μM (FIG. 8B). The affinity for 22 (the entire library) was 280 nM while the affinity for the empty cassette, 27, was 1.3 μM. Interactions between 21-FL and 27 likely occur between the deoxystreptamine ring and G•U pairs in the stem, which have been reported as aminoglycoside interacting motifs in other RNAs that bind aminoglycosides [41]. tRNAphe has also been shown to bind aminoglycosides [42] and binds 21-FL with a $K_d$ of 700 nM.

The dissociation constants for the two highest affinity loops from our resin-based selection were also determined using the fluorescence-based assay. (We state adenine across from a cytosine rather than A-C pair to denote that we do not know if these bases are indeed paired.) Both loops,

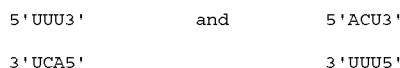

bind as tightly to 21-FL as the highest affinity 2×2 loop from the microarray selection with dissociation constants of 5±0.4 and 4±0.9 nM, respectively.

The affinities of the 1×1 nucleotide loops for 21-FL have a range of 5-12 nM (FIG. 12), and GG, AC, and CC loops are represented. It should be noted that previous experiments have also found that several aminoglycosides bind a 1×1 CC internal loop that is derived from the untranslated region in thymidylate synthase mRNA [43, 44]. In these previous reports, the dissociation constants for kanamycin B and tobramycin were 1.1 and 0.87 μM, respectively, in a buffer containing 1 mM $MgCl_2$ and $CaCl_2$, 150 mM NaCl, 5 mM KCl, and 20 mM HEPES (pH 7.5) [44]. We studied the binding of 21-FL to IL 24 in the same buffer and observed a similar affinity ($K_d$ of 0.21±0.04 μM) despite differences in closing base pairs and aminoglycoside structure. The difference in binding affinity between the two buffers is due to the presence of divalent metal ions and increased pH, which are well known to decrease the affinity of aminoglycosides to RNA [17].

Figure 13:
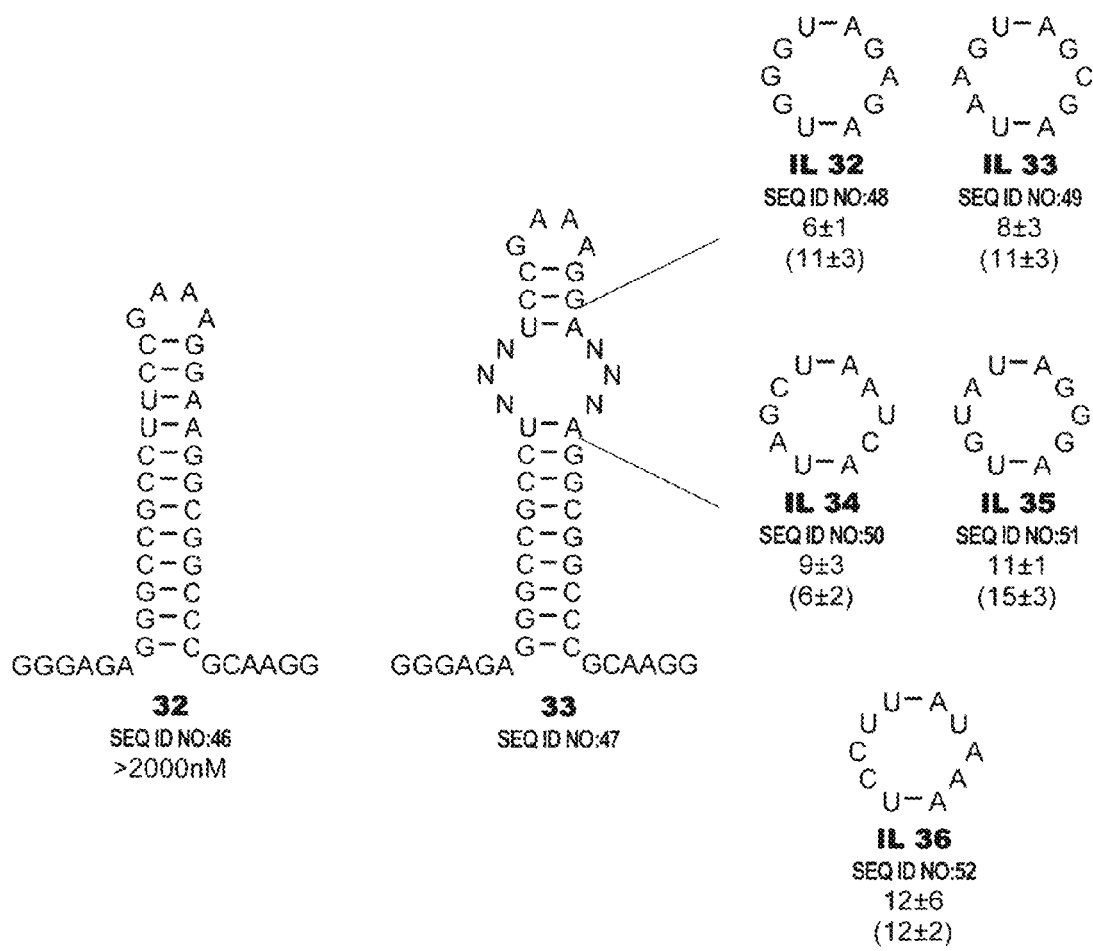
FIG. 13 shows secondary structure of the cassette with all GU and most AU pairs mutated to GC (32 (SEQ ID NO: 46)) used to determine if loop non-nearest neighbors contribute to binding affinity. The loop-closing base pairs were not mutated since they have been shown to affect loop structure. Oligonucleotide 33 (SEQ ID NO:47) is an RNA motif library (internal loop library) based on the cassette 32 with six randomized positions (N). The identities of 5 internal loops embedded in cassette 32 are shown (i.e., IL 32 (SEQ ID NO:48), IL 33 (SEQ ID NO:49), IL 34 (SEQ ID NO:50), IL 35 (SEQ ID NO:51), IL 36 (SEQ ID NO:52)). The dissociation constants for the loops in the mutated cassette are directly below the loop number and are reported in nanomoles per liter. The dissociation constants when the loops are displayed in 22 are in parentheses.

Because deoxystreptamine binds G•U pairs, the stem in 22 was mutated to assess if loop non-nearest neighbors contribute to binding affinity (FIG. 13). All G•U pairs and most AU pairs were mutated to GC. The loop closing base pairs (both AU pairs) were not mutated because previous reports have shown that closing base pairs can affect internal loop structure [45, 46]. Results from fluorescence experiments show that similar $K_d$ values are observed when the loops are displayed in either cassette (FIG. 13). Evidently, cassette nucleotides are not important for recognition of the selected loops by 21-FL.

To determine if selected loops have aminoglycoside preferences, the binding of five aminoglycosides, 21, kanamycin A, kanamycin B, tobramycin, and neamine (FIG. 7) to the pool of RNAs from spot 2+ (FIG. 10C) was probed using a competitive binding assay [43]. The $K_d$ values determined for 21, kanamycin A, and kanamycin B were 12 nM, 9 nM, and 12 nM, respectively. The pool bound approximately 9-fold more weakly to tobramycin ($K_d$=85 nM), consistent with the 3' hydroxyl group in ring I contributing to binding to the library of structures. Binding to neamine was even weaker as there was no change in fluorescence up to 500 nM neamine. We also tested a single RNA sequence identified to bind 21, IL 34, in the same manner. These experiments mirror the results of the pool of RNAs isolated from 2+, showing that 21, kanamycin A, and kanamycin B bind to IL 34 with $K_d$ values of 7 nM, 5 nM, and 5 nM, respectively. Binding to neamine and tobramycin was also much weaker. Both sets of experiments suggest that the recognition of 21 and related aminoglycosides (kanamycins A and B) is not due to simple charge-charge interactions; rather, there are specific interactions between the functional groups displayed by the aminoglycosides and the RNA. The weaker affinities for tobramycin and neamine suggest that both the 3' hydroxyl groups in ring I and ring III are important for binding. Interestingly, in both cases, 21 and 21-FL bind with the same affinity, showing that the fluorescence tag, the triazole, and the 6' $NH_2$ groups do not contribute significantly to binding. It is not surprising that the 6' $NH_2$ is not important for binding since structures were selected that bind a 6' acylated derivative of kanamycin A. It should be noted, however, that the 6' $NH_2$ forms important stabilizing contacts for aminoglycoside recognition of the bacterial rRNA A-site. When the 6' $NH_2$ is acetylated by AAC(6') resistance enzymes, binding to an oligonucleotide mimic of the bacterial rRNA A-site is reduced 1000-fold [47]. Therefore, there are differences in the molecular recognition of 21 to IL 34 and kanamycin A to the bacterial rRNA A-site.

Advantages of the Microarray Selection Platform.

The microarray selection platform is believed to have several advantages over other selection methods. One is the manner in which selected RNAs are harvested. In typical resin-based selections, selected RNAs are eluted with a high concentration of immobilized ligand which can introduce potential kinetic biases. Since the highest affinity RNAs are the most difficult to compete off, standard selection experiments can inadvertently miss the best binders. Capillary electrophoresis ("CE") SELEX has been developed to mitigate this problem [48]. The microarray method described in this Example harvests bound RNAs by simple excision of the agarose and gel extraction (FIG. 8B), thus avoiding potential kinetic biases. RNAs can be harvested precisely from the microarray surface; adjacent spots are unaffected and the RNAs are free from cross-contamination (FIG. 8B). Therefore, the RNA is suitable for downstream applications such as RT-PCR amplification and cloning, transcription of RT-PCR products, multiple rounds of selection, and determination of dissociation constants. Another important advantage of completing selections on a microarray platform is the ability to determine dose response on a single array (FIGS. 10A-10C). Standard selection methods only screen a library of targets against one compound at a single loading. Therefore, a separate experiment for each ligand loading is required to construct a dose response. In this study, higher affinity interactions were identified at a lower ligand loading (FIG. 10A). This result and the ones shown in FIGS. 11A-11B demonstrate that multiple selections can be completed on a single array surface. The number of parallel screens is limited by the number of compounds that can be placed onto an array surface from which bound RNAs can be subsequently isolated. With manual methods, the minimum number of compounds that can be screened is 50. It is likely that robotic arraying of compounds and using automated spot pickers to harvest bound RNAs could increase this number to at least hundreds of compounds. Finally, the microarray method requires a reduced amount of ligand compared to resin-based selections. Selected RNAs were amplified from positions where as little as 250 pmol of ligand were delivered to the array surface (FIGS. 10A and 10C, spot 2).

As discussed in Example 2 and elsewhere hereinabove, our long-range goal is to develop a database of RNA-ligand partners to facilitate the rational design of small molecules that target RNA. Clearly, new methods need to be developed because of the diverse number of RNA secondary structures and ligands that must be screened to construct such a database. Therefore, we developed a small molecule carbohydrate microarray platform to identify RNA-ligand interactions in which multiple selections and dose response can be completed in a single experiment. Traditional ligand discovery efforts screen a validated RNA drug target against a ligand library. This type of screen, however, gives little insight into potential off-target effects. Our microarray platform screens a library of RNAs to determine the RNA motif(s) preferred by a ligand. These preferences can then be used in RNA targeting applications while identifying potential bystander RNAs.

Once a wide variety of RNA motif ligand interactions have been identified, methods for modular assembly of ligands can be developed, such as those applied for polyamide recognition of Watson-Crick paired DNA [49]. Microarray-based screening is well suited for identifying ligands that will be used for modular assembly because chemistries used to anchor compounds onto surfaces can be used to link ligand modules together.

Example 6—A Small Molecule Microarray Platform to Select RNA Internal Loop-Ligand Interactions: Materials and Methods This Example 6 describes the materials and methods that were used in carrying out the experiments described in Example 5.
General Methods.
Chemicals were purchased from Sigma Aldrich, except radioactivity which was purchased from Perkin-Elmer. Chase RNA oligonucleotides were purchased from Dharmacon and were deprotected using the manufacturer's standard protocol. The chase DNA oligonucleotides (25 and 26, FIG. 3) and all DNA templates were purchased from IDT (Coralville, Iowa). The RNA 3×3 nucleotide internal loop library was transcribed from a DNA template using T7 RNA polymerase from a Strategene RiboMaxxx transcription kit [50]. Oligonucleotides were radioactively labeled on their 5' ends and purified as described in [51]. All solutions were made with DEPC-treated water.

Microarray Construction, Hybridization, and Harvesting Bound RNAs from the Agarose—Functionalized Array.

The 6'-N-5-hexynoate kanamycin A ligand (21) was spotted in 10 mM sodium phosphate, pH 7.5, 1 mM TCEP, 1 mM $CuSO_4$, 100 µM TBTA ligand [37], and 10% glycerol onto azide-displaying agarose slides [31] constructed as described in [40]. Azidoaminoglycoside (28-31) were immobilized onto alkyne-functionalized agarose surfaces as described in [52]. The alkyne-functionalized arrays were constructed as described hereinabove in Examples 1-3 except that propargylamine was used instead of 3-azidopropylamine. A grid affixed to the back of the microarray was used as a guide for spatial arraying. After immobilization, the grid was removed, and the slides were incubated overnight in a humidity chamber. The following morning, they were washed by submersion in 30 mL of hybridization buffer ("HB") (8 mM $Na_2HPO_{41}$ pH 7.0, 185 mM NaCl, and 1 mM EDTA) and then rinsed with water.

Microarrays were hybridized with a solution containing 5' end $^{32}$P-labeled RNA 3×3 nucleotide library (22) and chase oligonucleotides (FIG. 9). Chase oligonucleotides were used to ensure that RNA internal loop ligand interactions were probed. Each oligonucleotide (2 pmol of 5' end $^{32}$P-labeled RNA 3×3 internal loop library (22), 2 nmol of each chase oligonucleotide for experiments with 21 and 12 pmol of internally labeled 22 ($\alpha$-$^{32}$P-ATP, transcription with Strategene RNAMaxx kit using half of the suggested cold ATP and 4 µL of $^{32}$P-ATP or 40 µCi) and 20 nmol of each chase oligonucleotide for experiments with 28-31) was annealed separately in HB by heating at 95° C. for 1 min and cooling to RT on the benchtop. After cooling to RT, the solutions containing each oligonucleotide were mixed together and 40 µg/mL BSA was added in a total volume of 400 µL.

Prior to hybridization, arrays were pre-equilibrated with 400 µL of hybridization buffer containing 40 µg/mL of BSA for 5 min. The buffer was distributed evenly across the array surface using a custom-cut piece of PARAFILM™ that was placed over the applied solution. The PARAFILM™ and buffer were then removed. The solution containing 22 and chase oligonucleotides was applied to the array surface and distributed evenly as described. Slides were hybridized for approximately 30 min at RT. After incubation, the PARAFILM™ was removed from the slide, and the slide was submerged in 30 mL of hybridization buffer for 3 min with gentle agitation. The buffer was replaced, and the step was repeated. The residual buffer was removed from the array surface by applying a gentle stream of air, and the chip was allowed to remain at RT for 30 min to dry completely. The array was exposed to a phosphorimager plate that was scanned on a BioRad FX phosphorimager (FIG. 8B).

An autoradiogram of the array and a grid used to spot 21 were placed under the microarray as a template to excise the agarose at positions that captured RNA. A 200 mL aliquot of hybridization buffer was added to each position. After 30 s, excess buffer not absorbed by the surface was removed. The gel slice at that position was then excised using a toothpick, and the gel slice was placed into thin-walled PCR tubes with 18 µL of $H_2O$, 2 µL of 10×DNase I buffer, and 2 units of RNase-free DNase I (Promega). The tubes were vortexed and spun at 8000 g for 4 min to force the agarose to the bottom of the tube. The solution was incubated at 37° C. for 2 h, and the reaction was quenched by addition of 2 μL of 10×DNase stop solution. The sample was then incubated at 65° C. for 10 min to inactivate completely the DNase. Aliquots of this sample were RT-PCR amplified. We found that spot 2 (250 μmol of 21 delivered to the surface) was the lowest amount of ligand from which captured RNA can be amplified over the background (spot 3+) (FIGS. 10A and 10C). RT-PCR product was observed after 25 cycles of PCR following the RT step. Attempts were made to amplify positions where lower amounts of 21 were delivered, but they required >35 cycles for amplification. Under these conditions, RT-PCR product was observed from positions where 21 was not delivered. We therefore only processed the 2+ position.

RNA Internal Loop Ligand Interaction Affinity Measurements.

Direct Binding Assay Measurements. A fluorescence-based assay was used to determine binding affinities by monitoring the change in fluorescence intensity of 21-FL (FIG. 7) as a function of RNA concentration (up to 300 nM for selected loops; there is a nonspecific binding mode at concentrations >300 nM). RNA was annealed in 1×HB+40 μg/mL BSA at 60° C. for 5 min and allowed to slow cool on the benchtop. Then, 21-FL in 1×HB+40 μg/mL BSA was added to the solution of RNA to a final concentration of 10 nM, and the RNA serially diluted into 1×HB+40 μg/mL BSA+10 nM 21-FL. Samples were then placed into a well of a black 96-well plate and allowed to equilibrate for at least 30 min before reading fluorescence intensity on a Bio-Tek Synergy HT fluorescence plate reader (excitation, 485 nm; emission, 528; sensitivity, 70). Several different times were sampled to ensure that the fluorescence intensity was taken after these interactions reached equilibrium. A decrease in fluorescence intensity was observed as a function of RNA concentration. The binding measurements for each oligonucleotide were completed in at least triplicate. Dissociation constants were determined by curve fitting, and reported values are the mean of at least three experiments. The data were fit to:

$$I = I_o + 0.5\Delta0.5\Delta\varepsilon\{([21-FL]_o + [RNA]_o + K_t) - \\ (([21-FL]_o + [RNA] + K_t)^2 - 4[21-FL]_o[RNA]_o)^{0.5}\}$$

where I is the observed fluorescence intensity, $I_o$ is the fluorescence intensity in the absence of RNA, $\Delta\varepsilon$ is the difference between the fluorescence intensity in the absence of RNA and in the presence of infinite RNA concentration, $[21-FL]_o$ is the concentration of 21-FL, $[RNA]_o$ is the concentration of the selected internal loop or control RNA, and $K_t$ is the dissociation constant. We also plotted the change in fluorescence as a function of RNA equivalents for all selected internal loops. Saturation is observed between 0.8 and 1.3 equiv, suggesting a 1:1 stoichiometry. Control experiments were completed to ensure that fluorescein (the fluorescent tag) was not contributing to binding by incubating serial dilutions of IL 24 up to 3 μM with 10 nM FITC-triazole and 10 nM fluorescein.

Competition Binding Experiments.

A solution containing 75 nM IL 34 was refolded in 1× hybridization buffer+40 μg/mL BSA at 60° C. for 5 min. After slow cooling on the benchtop, 21-FL was added to a final concentration of 10 nM. The competing, unlabeled aminoglycoside was then added, and the resulting solution was serially diluted into 1× hybridization buffer+40 μg/mL BSA+10 nM 21-FL containing 75 nM IL 34. The solutions were equilibrated for 30 min at RT, and the fluorescence intensities were measured on a Bio-Tek HT fluorescence plate reader. Data were fit to:

$$\Theta = (1/(2[21-FL]))(K_t + (K_t/K_d)[C_t] + [RNA] + [21-FL] - \\ ((K_t + (K_t/K_d)[C_t] + [RNA] + [21-FL])^2 - 4[21-FL] \\ [RNA])^{0.5}) + A$$

where $\Theta$ is the fraction of 21-FL bound, $K_t$ is the dissociation constant determined for IL 34 from direct binding assays, $K_d$ is the dissociation constant of the competing, unlabeled aminoglycoside, $[C_t]$ is the concentration of competing aminoglycoside, and [RNA] is the concentration of IL 34.

Although the invention has been described in detail for the purpose of illustration, it is understood that such detail is solely for that purpose, and variations can be made therein by those skilled in the art without departing from the spirit and scope of the invention which is defined by the claims that are set forth below after the section entitled "References".

REFERENCES

1. Doudna, J. A. (2000) Structural genomics of RNA, Nat. Struct. Biol. 7 Suppl., 954-956.
2. Batey, R. T., et al. (1999) Tertiary motifs in RNA structure and folding, Angew. Chem., Int. Ed. Engl. 38, 2326-2343.
3. Zaug, A. J., et al. (1986) The intervening sequence RNA of tetrahymena is an enzyme, Science 231, 470-475.
4. Lagos-Quintana, M., et al. (2001) Identification of novel genes coding for small expressed RNAs, Science 294, 853-858.
5. Winkler, W., et al. (2002) Thiamine derivatives bind messenger RNAs directly to regulate bacterial gene expression, Nature 419, 952-956.
6. Gallego, J., et al. (2001) Targeting RNA with small molecule drugs: therapeutic promise and chemical challenges, Acc. Chem. Res. 34, 836-843.
7. Hamy, F., et al. (1997) An inhibitor of the Tat/TAR RNA interaction that effectively suppresses HIV-1 replication, Proc. Natl. Acad. Sci. U.S.A. 94, 3548-3553.
8. Mathews, D. H., et al. (2004) Incorporating chemical modification constraints into a dynamic programming algorithm for prediction of RNA secondary structure, Proc. Natl. Acad. Sci. U.S.A. 101, 7287-7292.
9. Mathews, D. H., et al. (1999) Expanded sequence dependence of thermodynamic parameters improves prediction of RNA secondary structure, J. Mol. Biol. 288, 911-940.
10. Woese, C. R., et al. (1980) Secondary structure model for bacterial 16S ribosomal RNA: phylogenetic, enzymatic and chemical evidence, Nucleic Acids Res. 8, 2275-2293.
11. Fourmy, D., et al. (1996) Structure of the A site of *Escherichia coli* 16S ribosomal RNA complexed with an aminoglycoside antibiotic, Science 274, 1367-1371.
12. Lynch, S. R., et al. (2003) Comparison of X-ray crystal structure of the 30S subunit-antibiotic complex with NMR structure of decoding site oligonucleotide-paromomycin complex, Structure (Cambridge, Mass., US) 11, 43-53.
13. Carter, A. P., et al. (2000) Functional insights from the structure of the 30S ribosomal subunit and its interactions with antibiotics, Nature 407, 340-348.
14. Kaul, M., et al. (2006) Aminoglycoside induced reduction in nucleotide mobility at the ribosomal RNA a-site as 14. a potentially key determinant of antibacterial activity, J. Am. Chem. Soc. 128, 1261-1271.
15. Kaul, M., et al. (2004) Fluorescence based approach for detecting and characterizing antibiotic-induced conformational changes in ribosomal RNA: comparing aminoglycoside binding to prokaryotic and eukaryotic ribosomal RNA sequences, J. Am. Chem. Soc. 126, 3447-3453.
16. Shandrick, S., et al. (2004) Monitoring molecular recognition of the ribosomal decoding site, Angew. Chem., Int. Ed. Engl. 43, 3177-3182.
17. Thomas, J. R., et al. (2006) Biochemical and thermodynamic characterization of compounds that bind to RNA hairpin loops: toward an understanding of selectivity, Biochemistry 45, 10928-10938.
18. Thomas, J. R., et al. (2005) Size-specific ligands for RNA hairpin loops, J. Am. Chem. Soc. 127, 12434-12435.
19. Thomas, J. R., et al. (2005) The relationship between aminoglycosides' RNA binding proclivity and their antiplasmid effect on an IncB plasmid combating drug-resistant bacteria: small molecule mimics of plasmid incompatibility as antiplasmid compounds, Biochemistry 44, 6800-6808.
20. Denap, J. C., et al. (2004) Combating drug-resistant bacteria: small molecule mimics of plasmid incompatibility as antiplasmid compounds, J. Am. Chem. Soc. 126, 15402-15404.
21. Klug, S. J., et al. (1994) All you wanted to know about SELEX, Mol. Biol. Rep. 20, 97-107.
22. Joyce, G. F. (1994) In vitro evolution of nucleic acids, Curr. Opin. Struct. Biol. 4, 331-336.
23. Griffey, R. H., et al. (1999) Determinants of aminoglycoside-binding specificity for rRNA by using mass spectrometry, Proc. Natl. Acad. Sci. U.S.A. 96, 10129-10133.
24. Swayze, E. E., et al. (2002) SAR by MS: a ligand based technique for drug lead discovery against structured RNA targets, J. Med. Chem. 45, 3816-3819.
25. He, Y., et al. (2004) Synthesis and evaluation of novel bacterial rRNA-binding benzimidazoles by mass spectrometry, Bioorg. Med. Chem. Lett. 14, 695-699.
26. Seth, P. P., et al. (2005) SAR by MS: discovery of a new class of RNA-binding small molecules for the hepatitis C virus: internal ribosome entry site IIA subdomain, J. Med. Chem. 48, 7099-7102.
27. Johnson, E. C., et al. (2003) Application of NMR SHAPES screening to an RNA target, J. Am. Chem. Soc. 125, 15724-15725.
28. MacBeath, G., et al. (1999) Printing small molecules as microarrays and detecting protein-ligand interactions en masse, J. Am. Chem. Soc. 121, 7967-7968.
29. Disney, M. D., et al. (2004) Aminoglycoside microarrays to explore interactions of antibiotics with RNAs and proteins, Chemistry 10, 3308-3314.
30. Ratner, D. M., et al. (2004) Tools for glycomics: mapping interactions of carbohydrates in biological systems, ChemBioChem 5, 1375-1383.
31. Afanassiev, V., et al. (2000) Preparation of DNA and protein micro arrays on glass slides coated with an agarose film, Nucleic Acids Res. 28, E66.
32. Dufva, M., et al. (2004) Characterization of an inexpensive, nontoxic, and highly sensitive microarray substrate, Biotechniques 37, 286-292294, 296.
33. Barrett, O. J., et al. (2006) Chemical microarrays to identify ligands that bind pathogenic cells, ChemBioChem 7, 1882-1885.
34. Bevilacqua, J. M., et al. (1998) Thermodynamic analysis of an RNA combinatorial library contained in a short hairpin, Biochemistry 37, 15877-15884.
35. Lato, S. M., et al. (1996) Screening chemical libraries for nucleic-acid-binding drugs by in vitro selection: a test case with lividomycin, Mol. Diversity. 2, 103-110.
36. Carlson, C. B., et al. (2003) Preferred RNA binding sites for a threading intercalator revealed by in vitro evolution, Chem. Biol. 10, 663-672.
37. Chan, T. R., et al. (2004) Polytriazoles as copper(I)-stabilizing ligands in catalysis, Org. Lett. 6, 2853-2855.
38. Kolb, H. C., et al. (2003) The growing impact of click chemistry on drug discovery, Drug Discovery Today 8, 1128-1137.
39. Kolb, H. C., et al. (2001) Click Chemistry: Diverse Chemical Function from a Few Good Reactions, Angew. Chem., Int. Ed. Engl. 40, 2004-2021.
40. Disney, M. D., et al. (2007) Using Selection to Identify and Chemical Microarray to Study the RNA Internal Loops Recognized by 6'-N-Acylated Kanamycin A, ChemBioChem 8, 649-656.
41. Yoshizawa, S., et al. (2002) Sequence-specific recognition of the major groove of RNA by deoxystreptamine, Biochemistry 41, 6263-6270.
42. Kirk, S. R., et al. (1999) tRNA(Phe) binds aminoglycoside antibiotics, Bioorg. Med. Chem. 7, 1979-1991.
43. Cho, J., et al. (2000) Specific binding of Hoechst 33258 to site 1 thymidylate synthase mRNA aminoglycoside antibiotics are able to specifically bind the 5'-untranslated region of thymidylate synthase messenger RNA, Nucleic Acids Res. 28, 2158-2163.
44. Harada, K., et al. (1999) Screening RNA-binding libraries using a bacterial transcription antitermination assay, Methods Mol. Biol. 118, 177-187.
45. Wu, M., et al. (1996) Solution structure of (rGCGGACGC) 2 by two-dimensional NMR and the iterative relaxation matrix approach, Biochemistry 35, 9677-9689.
46. SantaLucia, J., Jr., et al. (1993) Structure of (rGGCGAGCC) 2 in solution from NMR and restrained molecular dynamics, Biochemistry 32, 12612-12623.
47. Llano-Sotelo, B., et al. (2002) Aminoglycosides modified by resistance enzymes display diminished binding to the bacterial ribosomal aminoacyl-tRNA site, Chem. Biol. 9, 455-463.
48. Mendonsa, S. D., et al. (2004) In vitro evolution of functional DNA using capillary electrophoresis, J. Am. Chem. Soc. 126, 20-21.
49. Dervan, P. B. (2001) Molecular recognition of DNA by small molecules, Bioorg. Med. Chem. 9, 2215-2235.
50. Milligan, J. F., et al. (1989) Synthesis of small RNAs using T7 RNA polymerase, Methods Enzymol. 180, 51-62.
51. Disney, M. D., et al. (2000) Targeting a *Pneumocystis carinii* group I intron with methylphosphonate oligonucleotides: backbone charge is not required for binding or reactivity, Biochemistry 39, 6991-7000.
52. Disney, M. D., et al. (2007) An aminoglycoside microarray platform for directly monitoring and studying antibiotic resistance, Biochemistry 40, 11223-11230.
53. S. E. Osborne, A. D. Ellington, Chem. Rev. 1997, 97, 349ff.
54. Y. Wang, R. R. Rando, Chem. Biol. 1995, 2, 281ff.
55. Z. Shu, P. C. Bevilacqua, Biochemistry 1999, 38, 15369ff.
56. V. P. Antao, S. Y. Lai, I. Tinoco, Jr., Nucleic Acids Res. 1991, 19, 5901ff.
57. G. Werstuck, M. R. Green, Science 1998, 282, 296ff.

58. M. I. Recht, D. Fourmy, S. C. Blanchard, K. D. Dahlquist, J. D. Puglisi, J. Mol. Biol. 1996, 262, 421ff.
59. G. MacBeath, S. L. Schreiber, Science 2000, 289, 1760ff.
60. M. D. Disney, S. Magnet, J. S. Blanchard, P. H. Seeberger, Angew. Chem. Int. Ed. Engl. 2004, 43, 1591ff.
61. M. D. Disney, P. H. Seeberger, Chem. Biol. 2004, 11, 1701ff.
62. J. Roestamadji, I. Grapsas, S. Mobashery, J. Am. Chem. Soc. 1995, 117, 11060ff.
63. A. Vincze, R. E. Henderson, J. J. McDonald, N. J. Leonard, J. Am. Chem. Soc. 1973, 95, 2677ff.
64. C. Ehresmann, F. Baudin, M. Mougel, P. Romby, J. P. Ebel, B. Ehresmann, Nucleic Acids Res. 1987, 15, 9109ff.
65. D. Moazed, H. F. Noller, Nature 1987, 327, 389ff.
66. C. H. Wong, M. Hendrix, E. S. Priestley, W. A. Greenberg, Chem. Biol. 1998, 5, 397ff.
67. A. Krebs, V. Ludwig, O. Boden, M. W. Gobel, ChemBioChem 2003, 4, 972ff.
68. W. K. C. Park, M. Auer, H. Jaksche, C. H. Wong, J. Am. Chem. Soc. 1996, 118, 10150ff.
69. Y. Tor, ChemBioChem 2003, 4, 998ff.
70. N. Peyret, P. A. Seneviratne, H. T. Allawi, J. SantaLucia, Jr., Biochemistry 1999, 38, 3468ff.
71. J. SantaLucia, Jr., Proc. Natl. Acad. Sci. U.S.A. 1998, 95, 1460ff.
72. J. D. Puglisi, I. Tinoco, Jr., Methods Enzymol. 1989, 180, 304ff.
73. Y. Wang, K. Hamasaki, R. R. Rando, Biochemistry 1997, 36, 768ff.
74. D. J. Proctor, J. E. Schaak, J. M. Bevilacqua, C. J. Falzone, P. C. Bevilacqua, Biochemistry 2002, 41, 12062ff.
75. A. Sreedhara, J. A. Cowan, J. Biol. Inorg. Chem. 2001, 6, 166.

What is claimed is:

1. A method for identifying an RNA secondary structure motif which interacts with a ligand, said method comprising: providing a plurality of immobilized small molecule ligands immobilized on a support at two or more different loadings, wherein the two or more different loadings each comprise distinct amounts of immobilized small molecule ligands in the plurality of small molecule ligands, said two or more different loadings being immobilized at separate, discrete locations on the support, incubating the plurality of immobilized small molecule ligands with two or more chase oligonucleotides consisting of the sequence of SEQ ID NO: 4, SEQ ID NO: 5, SEQ ID NO: 6, SEQ ID NO:7, SEQ ID NO:8, SEQ ID NO:9, and SEQ ID NO:10, wherein the chase oligonucleotides are designed to compete with invariant regions of members of an RNA secondary structure motif library for binding to the plurality of immobilized ligands such that members of the RNA secondary structure motif library bind to the immobilized small molecule ligands in the plurality of immobilized small molecule ligands through variant regions, wherein the members of the RNA secondary structure motif library are selected from the group consisting of an internal loop library, a hairpin loop library, a bulge library, a multibranch loop library, a pseudoknot library, and combinations thereof, contacting the plurality of immobilized small molecule ligands with the RNA secondary structure motif library in the presence of the chase oligonucleotides under conditions effective for one or more members of the RNA secondary structure motif library to bind with one or more of the immobilized small molecule ligands, and wherein the RNA secondary structure motif library comprises at least 4 members; and identifying members of the RNA secondary structure motif library that are bound to particular immobilized small molecule ligands in the plurality of immobilized ligands, wherein said identifying the members of the RNA secondary structure motif library that are bound to each particular immobilized small molecule ligand comprises: amplifying and determining the sequence of the members of the RNA secondary structure motif library that are bound at the discrete location on the support corresponding to the particular immobilized small molecule ligand; and using a dose-response curve and a dissociation constant for each small molecule ligand loading to identify members of the RNA secondary structure motif library bound to lower small molecule ligand loading as having greater affinity for the small molecule ligand than members of the RNA secondary structure motif library bound to higher small molecule ligand loading, wherein the higher small molecule ligand loading and lower small molecule ligand loading comprise a serial dilution of the small molecule ligands, wherein the higher small molecule ligand loading comprises up to 100 nanomoles of the small molecule ligand, and wherein the lower ligand loading comprises not less than one femtomole of the small molecule ligand.

2. A method according to claim 1, wherein the support is an agarose support.

3. A method according to claim 1, wherein at least 10 small molecule ligands are immobilized on the support.

4. A method according to claim 1, wherein the RNA secondary structure motif library comprises at least 10 members.

5. A method according to claim 1, wherein the RNA secondary structure motif library comprises at least 100 members.

6. A method according to claim 1, wherein at least 10 small molecule ligands are immobilized on the support and wherein the RNA secondary structure motif library comprises at least 100 members.

7. A method according to claim 1, wherein said identifying the members of the RNA secondary structure motif library that are bound to a particular immobilized small molecule ligand comprises: harvesting members of the RNA secondary structure motif library that are bound at the discrete location on the support corresponding to the particular immobilized small molecule ligand; reverse transcriptase polymerase chain reaction (RT-PCR) amplifying the harvested members of the RNA secondary structure motif library; cloning the RT-PCR amplified members of the RNA secondary structure motif library; and sequencing the cloned RT-PCR amplified RNA members of the RNA secondary structure motif library.

* * * * *

SEQUENCE LISTING

```
<160> NUMBER OF SEQ ID NOS: 52

<210> SEQ ID NO 1
<211> LENGTH: 42
<212> TYPE: DNA
<213> ORGANISM: Artificial Sequence
<220> FEATURE:
<223> OTHER INFORMATION: primer

<400> SEQUENCE: 1
ggccgaattc taatacgact cactataggg agagggttta at                          42

<210> SEQ ID NO 2
<211> LENGTH: 12
<212> TYPE: DNA
<213> ORGANISM: Artificial Sequence
<220> FEATURE:
<223> OTHER INFORMATION: primer

<400> SEQUENCE: 2
ccttgctcca at                                                          12

<210> SEQ ID NO 3
<211> LENGTH: 46
<212> TYPE: RNA
<213> ORGANISM: Artificial Sequence
<220> FEATURE:
<223> OTHER INFORMATION: RNA motif library
<220> FEATURE:
<221> NAME/KEY: misc_feature
<222> LOCATION: (16)..(18)
<223> OTHER INFORMATION: "n" can be A, C, G, or U
<220> FEATURE:
<221> NAME/KEY: misc_feature
<222> LOCATION: (29)..(31)
<223> OTHER INFORMATION: "n" can be A, C, G, or U

<400> SEQUENCE: 3
gggagagggu uuaaunnnua cgaaaguann nauuggaucc gcaagg                     46

<210> SEQ ID NO 4
<211> LENGTH: 18
<212> TYPE: RNA
<213> ORGANISM: Artificial Sequence
<220> FEATURE:
<223> OTHER INFORMATION: stem sequence

<400> SEQUENCE: 4
```

-continued gggagauuug ggaauuac                                                18

<210> SEQ ID NO 5
<211> LENGTH: 18
<212> TYPE: RNA
<213> ORGANISM: Artificial Sequence
<220> FEATURE:
<223> OTHER INFORMATION: stem sequence

<400> SEQUENCE: 5
guaauuuccg gagcaagg                                                18

<210> SEQ ID NO 6
<211> LENGTH: 10
<212> TYPE: DNA
<213> ORGANISM: Artificial Sequence
<220> FEATURE:
<223> OTHER INFORMATION: hairpin loop sequence

<400> SEQUENCE: 6
cgcgaaagcg                                                         10

<210> SEQ ID NO 7
<211> LENGTH: 20
<212> TYPE: RNA
<213> ORGANISM: Artificial Sequence
<220> FEATURE:
<223> OTHER INFORMATION: chase oligonucleotide

<400> SEQUENCE: 7
cgcgcgcgcg cgcgcgcgcg                                              20

<210> SEQ ID NO 8
<211> LENGTH: 20
<212> TYPE: DNA
<213> ORGANISM: Artificial Sequence
<220> FEATURE:
<223> OTHER INFORMATION: chase oligonucleotide

<400> SEQUENCE: 8
gcgcgcgcgc gcgcgcgcgc                                              20

<210> SEQ ID NO 9
<211> LENGTH: 20
<212> TYPE: DNA
<213> ORGANISM: Artificial Sequence
<220> FEATURE:
<223> OTHER INFORMATION: chase oligonucleotide

<400> SEQUENCE: 9
atatatatat atatatatat                                              20

<210> SEQ ID NO 10
<211> LENGTH: 20
<212> TYPE: DNA
<213> ORGANISM: Artificial Sequence
<220> FEATURE:
<223> OTHER INFORMATION: chase oligonucleotide

<400> SEQUENCE: 10
tatatatata tatatatata                                              20

<210> SEQ ID NO 11
<211> LENGTH: 40
<212> TYPE: RNA
<213> ORGANISM: Artificial Sequence

```
<220> FEATURE:
<223> OTHER INFORMATION: cassette sequence

<400> SEQUENCE: 11
gggagagggu uuaauuacga aaguaauugg auccgcaagg                            40

<210> SEQ ID NO 12
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 12
gggagagggu uuaauuuuua cgaaaguaac uauuggaucc gcaagg                     46

<210> SEQ ID NO 13
<211> LENGTH: 46
<212> TYPE: RNA
<213> ORGANISM: Artificial Sequence
<220> FEATURE:
<223> OTHER INFORMATION: RNA displaying an internal look motif

<400> SEQUENCE: 13
gggagagggu uuaauaucua cgaaaguauu uauuggaucc gcaagg                     46

<210> SEQ ID NO 14
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 14
gggagagggu uuaaugauua cgaaagauua uauuggaucc gcaagg                     46

<210> SEQ ID NO 15
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 15
gggagagggu uuaaucuaua cgaaaguacu aauuggaucc gcaagg                     46

<210> SEQ ID NO 16
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 16
gggagagggu uuaauuccua cgaaaguaag uauuggaucc gcaagg                     46

<210> SEQ ID NO 17
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 17
gggagagggu uuaaugauua cgaaaguaaa gauuggaucc gcaagg                     46
```

```
<210> SEQ ID NO 18
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 18
gggagagggu uuaaucggua cgaaaguacu uauuggaucc gcaagg            46

<210> SEQ ID NO 19
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 19
gggagagggu uuaauccuua cgaaaguaaa gauuggaucc gcaagg            46

<210> SEQ ID NO 20
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 20
gggagagggu uuaaucgcua cgaaaguaac aauuggaucc gcaagg            46

<210> SEQ ID NO 21
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 21
gggagagggu uuaaugaaua cgaaaguaau aauuggaucc gcaagg            46

<210> SEQ ID NO 22
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 22
gggagagggu uuaauuauua cgaaaguacu aauuggaucc gcaagg            46

<210> SEQ ID NO 23
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 23
gggagagggu uuaaucgcua cgaaaguagc uauuggaucc gcaagg            46

<210> SEQ ID NO 24
<211> LENGTH: 46
<212> TYPE: RNA
<213> ORGANISM: Artificial Sequence
<220> FEATURE:
<223> OTHER INFORMATION: RNA sequence displaying internal loop motif
```

```
<400> SEQUENCE: 24
gggagagggu uuaaugugua cgaaaguaug aauuggaucc gcaagg            46

<210> SEQ ID NO 25
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 25
gggagagggu uuaauccuua cgaaaguaga gauuggaucc gcaagg            46

<210> SEQ ID NO 26
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 26
gggagagggu uuaauauuua cgaaaguaaa gauuggaucc gcaagg            46

<210> SEQ ID NO 27
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 27
gggagagggu uuaauugaua cgaaaguacg aauuggaucc gcaagg            46

<210> SEQ ID NO 28
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 28
gggagagggu uuaaucuuua cgaaaguacc gauuggaucc gcaagg            46

<210> SEQ ID NO 29
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 29
gggagagggu uuaauuagua cgaaaguaga uauuggaucc gcaagg            46

<210> SEQ ID NO 30
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 30
gggagagggu uuaaucuuua cgaaaguaga aauuggaucc gcaagg            46

<210> SEQ ID NO 31
```

```
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 31
gggagagggu uaauuagua cgaaaguagu gauuggaucc gcaagg          46

<210> SEQ ID NO 32
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 32
gggagagggu uaaugaaua cgaaaguauc uauuggaucc gcaagg          46

<210> SEQ ID NO 33
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 33
gggagagggu uaaucucua cgaaaguagg cauuggaucc gcaagg          46

<210> SEQ ID NO 34
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 34
gggagagggu uaauuagua cgaaaguauc gauuggaucc gcaagg          46

<210> SEQ ID NO 35
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 35
gggagagggu uaaucagua cgaaaguaug aauuggaucc gcaagg          46

<210> SEQ ID NO 36
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 36
gggagagggu uaauuuaua cgaaaguacu aauuggaucc gcaagg          46

<210> SEQ ID NO 37
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 37
```
gggagagggu uuaaugaaua cgaaaguaug aauuggaucc gcaagg         46

<210> SEQ ID NO 38
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 38
gggagagggu uuaauuacua cgaaaguacc gauuggaucc gcaagg         46

<210> SEQ ID NO 39
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 39
gggagagggu uuaauccuua cgaaaguagc cauuggaucc gcaagg         46

<210> SEQ ID NO 40
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 40
gggagagggu uuaauuacua cgaaaguauc gauuggaucc gcaagg         46

<210> SEQ ID NO 41
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 41
gggagagggu uuaaugggua cgaaaguaga gauuggaucc gcaagg         46

<210> SEQ ID NO 42
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 42
gggagagggu uuaauaagua cgaaaguagc gauuggaucc gcaagg         46

<210> SEQ ID NO 43
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 43
gggagagggu uuaauagcua cgaaaguaau cauuggaucc gcaagg         46

<210> SEQ ID NO 44
<211> LENGTH: 46
<212> TYPE: RNA

-continued

<213> ORGANISM: Artificial Sequence
<220> FEATURE:
<223> OTHER INFORMATION: RNA sequence displaying internal loop motif

<400> SEQUENCE: 44
gggagagggu uaauguaua cgaaaguagg gauuggaucc gcaagg            46

<210> SEQ ID NO 45
<211> LENGTH: 46
<212> TYPE: RNA
<213> ORGANISM: Artificial Sequence
<220> FEATURE:
<223> OTHER INFORMATION: RNA motif library

<400> SEQUENCE: 45
gggagagggu uaauccuua cgaaaguaua aauuggaucc gcaagg            46

<210> SEQ ID NO 46
<211> LENGTH: 40
<212> TYPE: RNA
<213> ORGANISM: Artificial Sequence
<220> FEATURE:
<223> OTHER INFORMATION: cassette sequence

<400> SEQUENCE: 46
gggagagggc cgccuuccga aaggaaggcg gcccgcaagg            40

<210> SEQ ID NO 47
<211> LENGTH: 46
<212> TYPE: RNA
<213> ORGANISM: Artificial Sequence
<220> FEATURE:
<223> OTHER INFORMATION: RNA sequence displaying internal loop motif
<220> FEATURE:
<221> NAME/KEY: misc_feature
<222> LOCATION: (16)..(18)
<223> OTHER INFORMATION: "n" can be A, C, G, or U
<220> FEATURE:
<221> NAME/KEY: misc_feature
<222> LOCATION: (29)..(31)
<223> OTHER INFORMATION: "n" can be A, C, G, or U

<400> SEQUENCE: 47
gggagagggc cgccunnnuc cgaaaggann naggcggccc gcaagg            46

<210> SEQ ID NO 48
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 48
gggagagggc cgccuggguc cgaaaggaga gaggcggccc gcaagg            46

<210> SEQ ID NO 49
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 49
gggagagggc cgccuaaguc cgaaaggagc gaggcggccc gcaagg            46

<210> SEQ ID NO 50
<211> LENGTH: 46

```
<212> TYPE: RNA
<213> ORGANISM: Artificial Sequence
<220> FEATURE:
<223> OTHER INFORMATION: RNA sequence displaying internal loop motif

<400> SEQUENCE: 50
gggagagggc cgccuagcuc cgaaaggaau caggcggccc gcaagg            46

<210> SEQ ID NO 51
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 51
gggagagggc cgccuguauc cgaaaggagg gaggcggccc gcaagg            46

<210> SEQ ID NO 52
<211> LENGTH: 46
<212> TYPE: RNA
<213> ORGANISM: Artificial Sequence
<220> FEATURE:
<223> OTHER INFORMATION: RNA sequence displaying internal loop motif

<400> SEQUENCE: 52
gggagagggc cgccuccuuc cgaaaggaua aaggcggccc gcaagg            46
```